United States Patent
Wybo et al.

(10) Patent No.: US 11,980,474 B1
(45) Date of Patent: May 14, 2024

(54) INTRAOPERATIVE NEURAL MONITORING SYSTEM UTILIZING WAVELET-BASED EVENT DETECTION

(71) Applicant: NEURALYTIX, LLC, Brighton, MI (US)

(72) Inventors: Christopher Wybo, Brighton, MI (US); David S. Nay, Novi, MI (US); Darren P. Scarfe, LaSalle (CA); Lukas T. Scarfe, LaSalle (CA); Samantha J. O'Neil, Windsor (CA)

(73) Assignee: NEURALYTIX, LLC, Brighton, MI (US)

( * ) Notice: Subject to any disclaimer, the term of this patent is extended or adjusted under 35 U.S.C. 154(b) by 0 days.

(21) Appl. No.: 18/320,439

(22) Filed: May 19, 2023

Related U.S. Application Data

(60) Provisional application No. 63/485,476, filed on Feb. 16, 2023.

(51) Int. Cl.
 *A61B 5/395* (2021.01)
 *A61B 5/00* (2006.01)
 *A61B 5/11* (2006.01)

(52) U.S. Cl.
 CPC ............ *A61B 5/395* (2021.01); *A61B 5/1107* (2013.01); *A61B 5/7221* (2013.01); *A61B 5/726* (2013.01)

(58) Field of Classification Search
 CPC ..... A61B 5/395; A61B 5/1107; A61B 5/7221; A61B 5/726
 See application file for complete search history.

(56) References Cited

U.S. PATENT DOCUMENTS

| | | | |
|---|---|---|---|
| 6,132,387 A | * | 10/2000 | Gozani .............. A61B 5/742 600/554 |
| 7,277,759 B2 | | 10/2007 | Overstreet et al. |
| 8,343,065 B2 | | 1/2013 | Bartol et al. |

(Continued)

FOREIGN PATENT DOCUMENTS

| | | |
|---|---|---|
| CA | 2595286 A | 1/2006 |
| CN | 113509644 A | 10/2021 |
| JP | 2018501024 A | 1/2018 |

OTHER PUBLICATIONS

Hong-liu Yu et al., "MMG Signal and Its Applications in Prosthesis Control", © 2010 START Centre, 4 pages, https://dl.acm.org/doi/pdf/10.5555/1926058.1926116#:~: text=Surface%20mechanomyogram%20signal%20(MMG)%20is,the%20surface%20of%20the%20skin).*

*Primary Examiner* — Alexander Satanovsky
(74) *Attorney, Agent, or Firm* — Quinn IP Law

(57) ABSTRACT

An intraoperative neural monitoring system for use during a surgical procedure on a subject includes a mechanical sensor and a processor. The mechanical sensor is configured to monitor a physical motion of a muscle of the subject and provide a mechanomyography (MMG) signal corresponding to the monitored physical motion. The processor is configured to receive the MMG signal, apply a wavelet transform to the MMG signal, and determine, from the output of the wavelet transform, if the monitored physical motion of the muscle is an artificially induced neuromuscular response that is attributable to an applied electrical stimulus. If the processor determines that the monitored physical motion of the muscle is an artificially induced neuromuscular response, it then provides an indication to a user.

8 Claims, 8 Drawing Sheets

(56) References Cited

U.S. PATENT DOCUMENTS

| | | |
|---|---|---|
| 9,301,711 B2 | 4/2016 | Bartol et al. |
| 9,604,065 B2 | 3/2017 | Rockweiler et al. |
| 10,869,616 B2 | 12/2020 | Wybo et al. |
| 11,712,566 B2 | 8/2023 | Gharibans et al. |
| 2006/0200121 A1* | 9/2006 | Mowery ............ A61B 18/1477 606/41 |
| 2007/0055151 A1* | 3/2007 | Shertukde .......... A61B 5/02007 600/437 |
| 2011/0196262 A1* | 8/2011 | McLeod ................ A61B 5/224 600/587 |
| 2011/0230782 A1 | 9/2011 | Bartol et al. |
| 2011/0230783 A1 | 9/2011 | Bartol et al. |
| 2011/0237974 A1 | 9/2011 | Bartol et al. |
| 2013/0072811 A1 | 3/2013 | Bartol et al. |
| 2013/0072812 A1 | 3/2013 | Bartol et al. |
| 2013/0123659 A1 | 5/2013 | Bartol et al. |
| 2013/0253364 A1 | 9/2013 | Bartol et al. |
| 2013/0253533 A1 | 9/2013 | Bartol et al. |
| 2014/0058284 A1 | 2/2014 | Bartol et al. |
| 2014/0058288 A1 | 2/2014 | Bartol et al. |
| 2014/0058283 A1 | 3/2014 | Bartol et al. |
| 2014/0073986 A1 | 3/2014 | Bartol et al. |
| 2014/0088612 A1 | 3/2014 | Bartol et al. |
| 2015/0051506 A1* | 2/2015 | Wybo .................. A61B 5/1109 600/554 |
| 2015/0051507 A1 | 2/2015 | Wybo et al. |
| 2015/0088029 A1 | 3/2015 | Wybo |
| 2015/0233892 A1 | 8/2015 | Van Berkel |
| 2017/0020450 A1 | 1/2017 | Wybo et al. |
| 2017/0020451 A1 | 1/2017 | Wybo |
| 2017/0020611 A1 | 1/2017 | Wybo et al. |
| 2018/0092559 A1* | 4/2018 | Wybo .................. A61B 5/7425 |
| 2018/0360336 A1* | 12/2018 | O'Brien .................. A61B 5/24 |
| 2019/0269342 A1 | 9/2019 | Wybo |
| 2019/0365288 A1 | 12/2019 | Wybo et al. |
| 2020/0113485 A1 | 4/2020 | Wybo et al. |
| 2020/0114148 A1 | 4/2020 | Wybo |
| 2020/0237296 A1* | 7/2020 | Schiff .................... A61B 5/383 |
| 2021/0060337 A1 | 3/2021 | Wybo et al. |
| 2021/0093228 A1 | 4/2021 | Wybo et al. |
| 2022/0331586 A1* | 10/2022 | Offutt ................ A61N 1/36007 |
| 2022/0370020 A1 | 11/2022 | Wybo et al. |
| 2022/0401000 A1 | 12/2022 | Wybo |
| 2023/0072423 A1* | 3/2023 | Osborn .................. G16H 20/30 |

\* cited by examiner

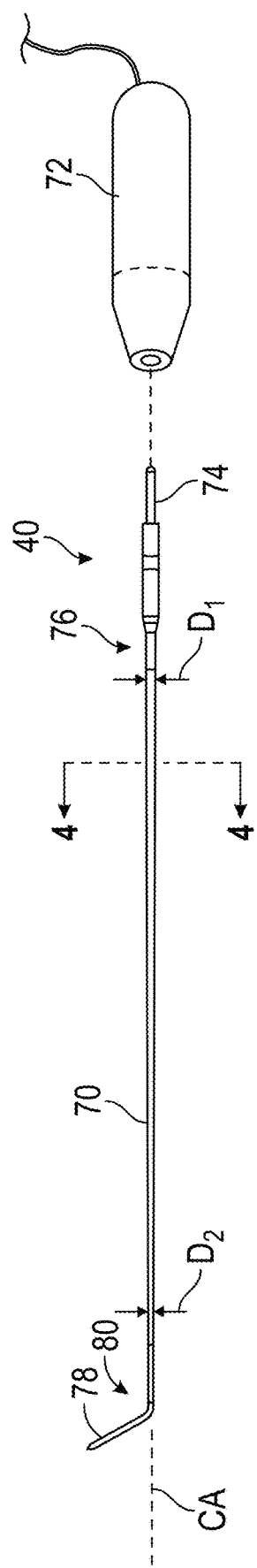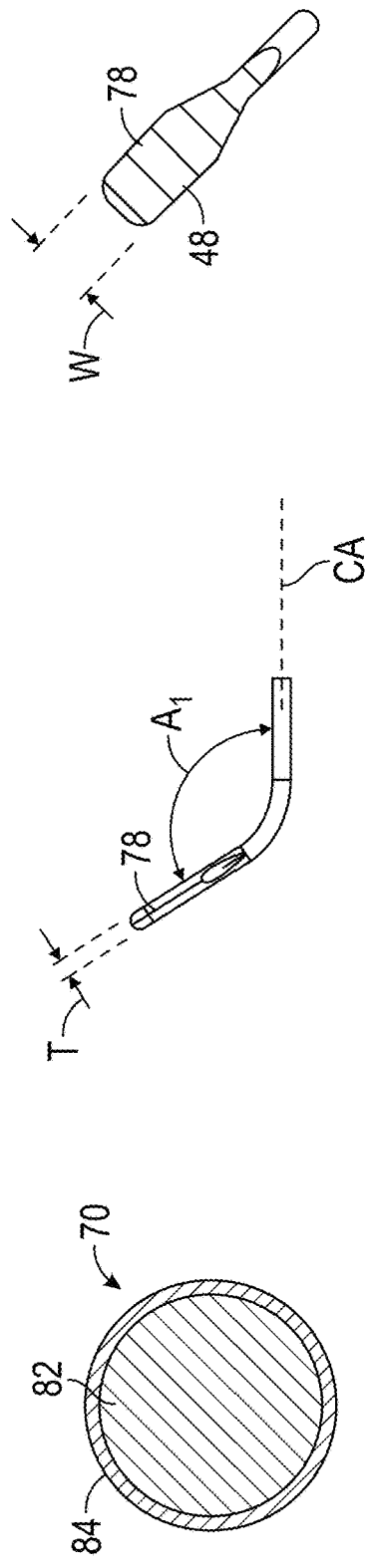
FIG. 3
FIG. 4
FIG. 5
FIG. 6

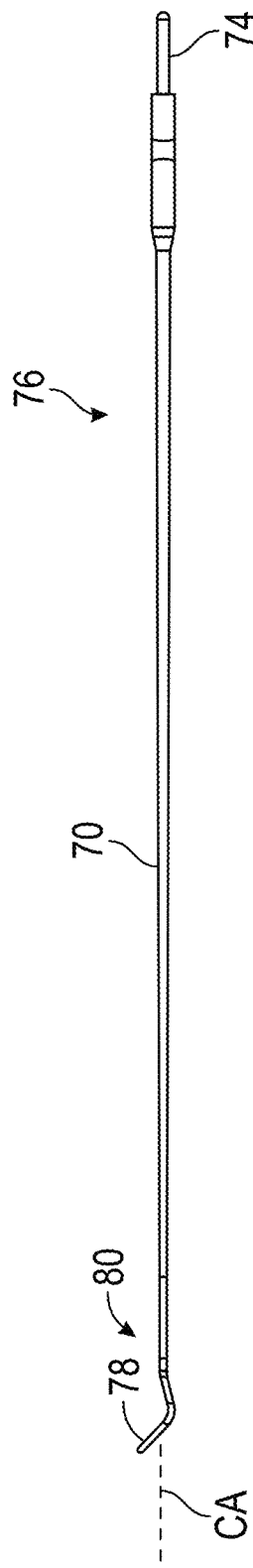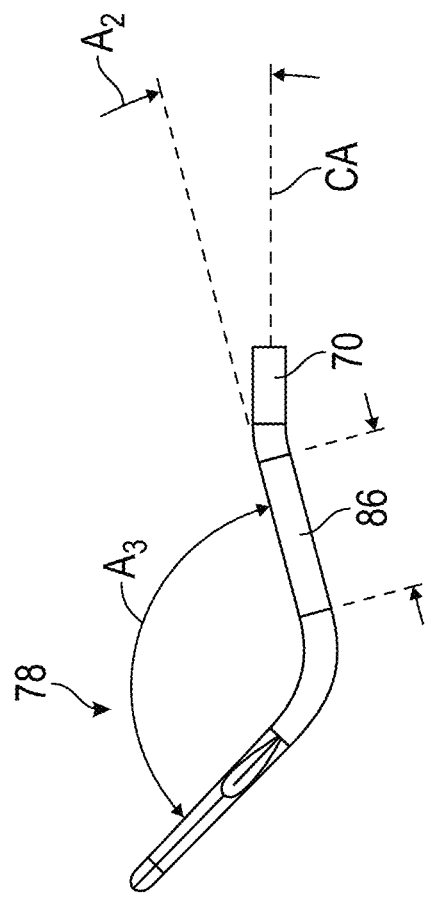
FIG. 7
FIG. 8

INTRAOPERATIVE NEURAL MONITORING SYSTEM UTILIZING WAVELET-BASED EVENT DETECTION

CROSS-REFERENCE TO RELATED APPLICATIONS

The present disclosure claims the benefit of priority from U.S. Provisional Patent No. 63/485,476, filed 16 Feb. 2023, which is incorporated by reference in its entirety and for all that it discloses.

TECHNICAL FIELD

The present disclosure relates generally to systems and techniques for intraoperatively identifying the presence and/or functioning of nerves.

BACKGROUND

Mechanomyography (MMG) is a technique for assessing muscle activity by detecting and analyzing the mechanical vibrations generated by muscle fibers during contraction. MMG has gained increasing attention in recent years as a potential alternative to electromyography (EMG) for evaluating neuromuscular function, as it is less susceptible to certain artifacts and electrical interference that may affect EMG signals.

Despite the potential advantages of MMG, its adoption has been limited, primarily due to challenges associated with MMG signal analysis and interpretation. MMG signals are often complex and may include various environmental or subject-created artifacts and physiological sources of variability that can hinder accurate characterization.

BRIEF DESCRIPTION OF THE DRAWINGS

FIG. 3 is a partially exploded schematic side view of a selectively electrifiable nerve stimulator for applying an electrical stimulus to a nerve or nerve root during a surgical procedure.

FIG. 4 is a schematic cross-sectional view of the nerve stimulator of FIG. 3, taken along line 4-4.

FIG. 5 is a partial side view of the stimulator tip of the nerve stimulator of FIG. 3.

FIG. 6 is a partial top view of the stimulator tip of the nerve stimulator of FIG. 3.

FIG. 7 is schematic side view of a selectively electrifiable nerve stimulator for applying an electrical stimulus to a nerve or nerve root during a surgical procedure.

FIG. 8 is a is a partial side view of the stimulator tip of the nerve stimulator of FIG. 7.

DETAILED DESCRIPTION

Figure 1:
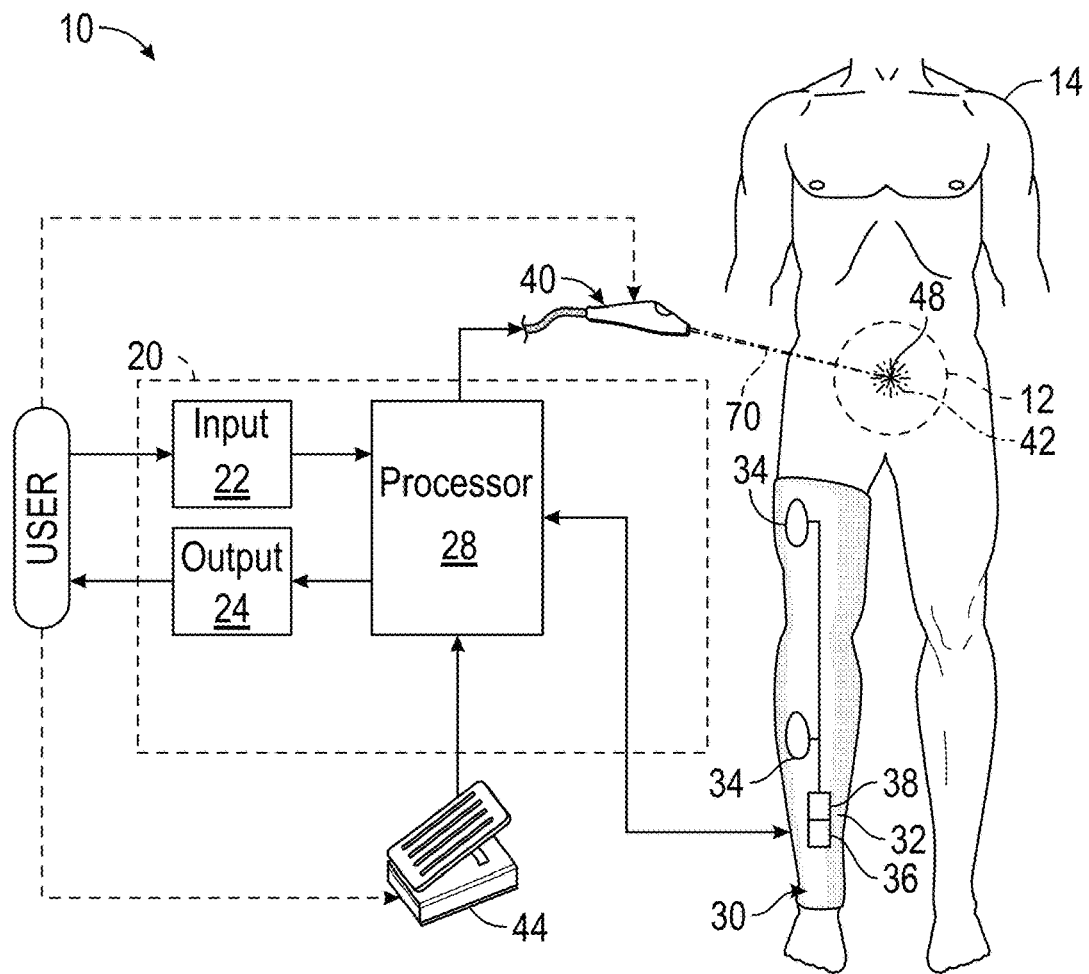
FIG. 1 is a schematic diagram of a neural monitoring system, for detecting an artificially-induced neuromuscular response of a subject during a surgical procedure

Referring to the drawings, wherein like reference numerals are used to identify like or identical components in the various views, FIG. 1 schematically illustrates a neural monitoring system 10 that may have particular use during a surgical procedure. As will be discussed, in some embodiments, the neural monitoring system 10 may be used within some surgical contexts to identify the presence of one or more nerves within an intracorporeal treatment area 12 of a subject 14. Further, in some embodiments, the neural monitoring system 10 may be used to intraoperatively assess the functioning or health of a nerve, such as during a decompression-type surgical procedure.

Regardless of the specific end use, the present neural monitoring system 10 operates by monitoring one or more muscles of the subject 14 for a muscular response that is indicative of a stimulus-induced depolarization of a nerve (i.e., an artificially induced neuromuscular response). If the system 10 detects a response of the muscle to the applied stimulus, then parameters such as the magnitude and waveform of the muscle response, the magnitude and/or timing of the applied stimulus, and/or the context of the procedure may be analyzed to provide intraoperative alerts and/or real-time diagnostics to a surgeon about a state of the procedure or status of a nerve within the patient.

As used herein, an "artificially induced neuromuscular response" is a response of a muscle to an artificial/non-biological stimulus applied to a nerve innervating that muscle. In general, the response is "artificially induced" because the nerve is depolarized directly by the stimulus, instead of, for example, the stimulus being received through an intermediate sensory means (e.g., sight, sound, taste, smell, and touch). An example of a stimulus that may cause an "artificially-induced" muscle response may include an electrical current applied directly to the nerve or to intracorporeal tissue or fluid immediately surrounding the nerve. In such an example, if the applied electrical current is sufficiently strong and/or sufficiently close to the nerve, it may cause the nerve to involuntarily depolarize (resulting in a corresponding contraction of the muscle or muscles innervated by that nerve). Other examples of such "artificial stimuli" may involve mechanically-induced depolarization (e.g., physically stretching or compressing a nerve, such as with a tissue retractor), thermally-induced depolarization (e.g., through ultrasonic cautery), or chemically-induced depolarization (e.g., through the application of a chemical agent to the tissue surrounding the nerve).

During an artificially induced neuromuscular response, a muscle innervated by the artificially depolarized nerve may physically contract or relax (i.e., a mechanical response) and/or the electrical potential throughout the muscle may be altered. Mechanical responses may primarily occur along a longitudinal direction of the muscle (i.e., a direction aligned with the constituent fibers of the muscle), though may further result in a respective swelling/relaxing of the muscle in a lateral direction (which may be substantially normal to the skin for most skeletal muscles). This local movement of the muscle during an artificially-induced mechanical muscle response may be measured relative to the position of the muscle when in a non-stimulated state.

The neural monitoring system 10 may generally include a host system 20 and one or more sensing devices 30 that coordinate to monitor muscles for a response to a stimulus 42 provided by a stimulator 40. As schematically shown in FIG. 1, the host system 20 may include one or more input devices 22 that are operative to receive information from the surgeon, one or more output devices 24 that are operative to communicate alerts or to provide informational feedback to the surgeon, and a processor 28 that is operative to at least manage the flow of information between the input devices 22, output devices 24, sensing devices 30, and stimulator 40.

In general, the one or more input devices 22 may include a keyboard, a mouse, and/or a digitizer provided with a touch-screen display. These devices may receive pre-operative case information or may permit a surgeon to alter various intraoperative parameters, alarm limits, or other case information before or during a procedure. In some embodiments, the stimulator 40 and/or a foot pedal 44 may provide additional input to the host system 20. This input may be in the form of an analog or digital signal that is indicative of the delivery and/or magnitude of a stimulus. The output device 24 may include, for example, a visual display such as an LED/LCD display, one or more indicator lights, or speakers capable of providing an audible alert to the surgeon. Examples of display screens that may be displayed via the output device 24 are provided in FIGS. 11-12.

Sensing Device

The sensing device 30 is the portion of the system 10 that directly contacts the subject 14 and is responsible for, at a minimum, sensing/detecting responses of the subject's muscles to the applied stimulus. The sensing device 30 may include a carrier material 32 that is operative to be secured to the external skin surface of the subject 14, and at least one neuromuscular sensor (NMS) 34 that is coupled with the carrier material 32 and is operative to monitor a muscular response of the subject 14. In some embodiments, each neuromuscular sensor 34 may include its own carrier material that is operative to mechanically couple the NMS 34 to the skin of the subject. In other embodiments, two or more neuromuscular sensors 34 may be held in mechanical contact with the skin of the subject 14 via a common carrier material 32 such as a large patch or band. Likewise, while the various neuromuscular sensors may each monitor different muscles/muscle groups, in some embodiments, multiple neuromuscular sensors may be joined together via a common wiring harness for the purpose of simplifying the initial setup.

Within the context of the present system 10, the purpose of the carrier material 32 is to hold the one or more neuromuscular sensors 34 in direct mechanical communication with the skin of the subject 14. In some embodiments the carrier material 32 may encapsulate and/or form a sterile barrier around the NMS 34. This may promote cost-effective reusability of the NMS 34 without subjecting it to the same sterilization requirements as if it were directly within the sterile field (i.e., absent a suitable barrier material). Suitable carrier materials may include, for example, adhesive pads, pocketed patches, cuffs, and/or sleeves. In some embodiments, the carrier material 32 may be a separate therapeutic or diagnostic device that is already common in surgical applications. For example, in a spinal procedure involving one or more of the L2-S1 vertebrae, it is known that nerve roots innervating the leg muscles may lie within the surgical area. During such procedures, however, compression-type anti-embolism stockings (Thrombo-Embolic-Deterrent ("TED") hose) are typically provided around a subject's legs and feet to discourage blood clot formation. Thus, in one embodiment the carrier material 32 may be an elastic sleeve/stocking configured to apply a compressive force to the subject's leg when worn, thus eliminating the need for separate TED hose. Such a compression against the subject may present itself as an elastic tension/strain in the carrier material itself (also referred to as a "tension fit"). In surgical procedures performed higher on the spine, the carrier material 32 may include, for example, a blood pressure cuff worn around the subject's arm (or else may include functionality similar to that of a standard blood pressure cuff). In these examples, the carrier material 32 serves a function outside of that of a dedicated neuromuscular sensing device, and thus provides efficiencies in pre-op preparation and planning, while also allowing monitoring access on sometimes crowded limbs.

Figure 2:
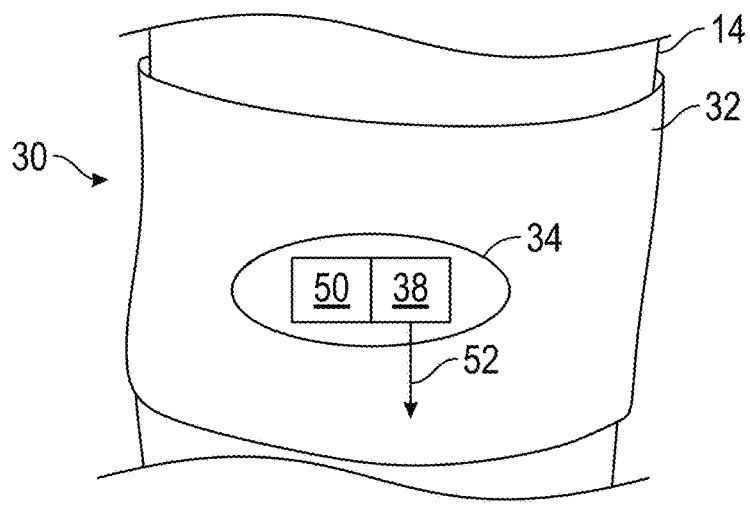
FIG. 2 is a schematic side view of a sensing device for use with a neural monitoring system.

In various embodiments, such as shown in FIG. 2, each NMS 34 may comprise a mechanical sensor 50 that is operative to monitor the relative movement of the muscle that the NMS 34 is most closely coupled with. Such mechanical sensors 50 may include, for example, a strain gauge, a pressure/force transducer, a position encoder, an accelerometer, a piezoelectric material, or any other transducer or combination of transducers that may convert a physical motion into a variable analog or digital electrical signal. In some embodiments, a neuromuscular sensor 34 may alternatively or additionally include one or more transdermal electrodes, needle electrodes, or other such sensors that may be operative to monitor mechanical or electrical response parameters of the subject.

In some embodiments, each neuromuscular sensor 34 (or collection of neuromuscular sensors 34, such as shown in FIG. 1) may include a local processor 38 that is in communication with the mechanical sensor 50 of that NMS 34. Such local processors 38 may be configured to, for example, preprocess and/or filter data acquired from the mechanical sensor 50 and transmit an MMG output signal 52 to the host system 20 (i.e., where the MMG output signal may be representative of the output or filtered output of the mechanical sensor 50). In some configurations these local processors 38 may even be capable of performing event detection algorithms (as will be discussed in greater detail below) to determine if a sensed movement is a result of a stimulus-induced depolarization of a nerve. This local processor 38 may further include suitable communication circuitry to facilitate unidirectional or bidirectional digital communication with the host system 20.

In general, processors used with the present system 10 (e.g., processors 28, 38) may each be embodied as one or multiple digital computers, data processing devices, and/or digital signal processors (DSPs), which may have one or more microcontrollers or central processing units (CPUs), read only memory (ROM), random access memory (RAM), electrically-erasable programmable read only memory (EEPROM), flash memory, high-speed clocks, analog-to-digital (A/D) circuitry, digital-to-analog (D/A) circuitry, input/output (I/O) circuitry, and/or signal conditioning and buffering electronics.

Stimulator Probe

As noted above, the system 10 may further include one or more elongate medical instruments 40 (i.e., stimulators 40) that are capable of selectively providing a stimulus 42 within the intracorporeal treatment area 12 of the subject 14. For example, in one configuration, the elongate medical instrument 40 may include an elongate body (e.g., a ball-tip probe, k-wire, or needle) that has an electrode 48 disposed on a distal end portion. The electrode 48 may be selectively electrified, at either the request of a user/surgeon, or at the command of the processor 28, to provide an electrical stimulus 42 to intracorporeal tissue of the subject. In other configurations, the elongate medical instrument 40 may comprise a dilator, retractor, clip, cautery probe, pedicle screw, robotic end effector, or any other medical instrument that may be used in an invasive medical procedure. Regardless of the instrument, if the intended artificial stimulus is an electrical current, the instrument 40 may include a selectively electrifiable electrode 48 disposed at a portion of the instrument that is intended to contact tissue within the intracorporeal treatment area 12 during the procedure. In some embodiments, the electrode 48 may be a distinct element, such as a gold contact that is overlaid onto the instrument. In other embodiments, the electrode 48 may simply be an uninsulated/exposed portion of the instrument 40 that is electrically conductive and able to outwardly transmit an electrical current to surrounding tissue/fluids.

FIGS. 3-6 schematically illustrate one embodiment of a stimulator 40 that may be used, for example, to access and electrically stimulate a nerve root that is compressed within a foramen of the spine (i.e., either the vertebral foramen that contains the spinal column, or the neural/intervertebral foramen where the nerve exits the spine). This stimulator 40 is particularly configured to gain direct access to the nerve root within the foramen via its specialized geometry, which is capable of extending around a portion of the spinal lamina either from an upper (superior) or lower (inferior) direction.

As generally shown, the stimulator 40 includes an elongate body 70, a handle 72 and/or handle connector 74 at a proximal end portion 76 of the body 70, and a stimulator tip 78 at a distal end portion 80 of the body 70. While the handle connector 74 and stimulator tip 78 may be electrically conductive and in electrical communication with each other, the exterior surface of the body 70 between the handle connector 74 and the stimulator tip 78 may be non-conductive. For example in one embodiment, the elongate body 70 may be substantially formed from a stainless steel material such as a 304, 316 or 316L type stainless steel alloy. As generally shown in the cross-sectional view provided in FIG. 4, surrounding/enveloping the stainless steel core 82 may be a layer of an electrically insulating material 84 that extends between the stimulator tip 78 and the handle connector 74. In some embodiments, this electrically insulating material 84 may comprise an oxide layer (e.g., such as may be present through an anodizing process), a polymer, a glass, or a ceramic material. In one embodiment, the insulating material 84 may comprise a deposited parylene coating. In other embodiments, the insulating material 84 may comprise a polymer such as, and without limitation, a polyvinylidene fluoride (PVDF), a polyether block amide (PEBA), a high-density polyethylene (HDPE), a cross-linked acrylated olefin, a polytetrafluoroethylene (PTFE), a fluorinated ethylene propylene (FEP), or a polyethylene terephthalate (PET).

Referring again to FIG. 3, to provide increased feel and tactile response through nerve-dense regions and around bony anatomy (which may not be directly visible due to such anatomy being on an internal side of the spinal lamina) at least a portion of the body 70 (and specifically the metallic core 82 of the body 70) may have a tapered cross-sectional profile that provides greater flexibility to the instrument at or near the distal end portion 80. Such a tapered profile may transition, for example from a maximum body diameter D1 of about 1.8 mm to about 2.2 mm (or about 1.9 mm to about 2.1 mm, or even about 2.0 mm) to a minimum body diameter D2 of about 0.7 mm to about 0.9 mm (or about 0.75 mm to about 0.85 mm, or even about 0.8 mm). In one configuration, the taper may be a constant taper that results in at least a 50% reduction in body diameter over a length of at least about 75 mm.

FIGS. 5-6 present an enlarged image of the stimulator tip 78 and distal end portion 80 of the body 70. As shown, in this embodiment, the stimulator tip 78 has narrow thickness T that is designed to more easily access tight spaces and a comparatively wider width W to ensure optimal electrical contact with the nerve. In some embodiments, the thickness T may be between about 0.4 mm and about 0.8 mm, (or between about 0.4 mm and about 0.6 mm, or even about 0.5 mm). In one embodiment, the tip 78 may have a width to thickness ratio of between about 3.5:1 and about 4.5:1, and a total stimulated surface area of between about 10 $mm^2$ and about 20 $mm^2$.

As best shown in FIGS. 3 and 5, the stimulator tip 78 and distal end portion 80 of the elongate body 70 may have a unique bend geometry that enables the electrically conductive tip to reach around the lamina and access a nerve within a foramen. More specifically, the stimulator tip 78 may be pitched at an angle A1 of between about 30 and about 80 degrees (or between about 40 and about 60 degrees, or even about 45 degrees) relative to a central axis CA of the body 70 (i.e., where the stimulator tip 78 is pitched in a tangential direction that is parallel to the thickness).

In some embodiments, to provide an adequate bend angle while also minimizing the required size of the working corridor used to access the spine, the distal end portion may include a compound bend such as shown in FIGS. 7-8. In this embodiment, the stimulator tip 78 may be joined with the body 70 via a neck portion 86 that is pitched at an angle A2 of between about 10 and about 25 degrees (or between about 12 and about 17 degrees, or even about 15 degrees) relative to a center axis CA of the body, while the stimulator tip 78 is then bent in the same plane as this "neck bend" to form an angle A3 between the stimulator tip 78 and the neck 86 of between about 100 and about 140 degrees (or between about 115 and about 125 degrees, or even about 120 degrees).

General Operation

During a surgical procedure, the user/surgeon may selectively administer the stimulus to intracorporeal tissue within the treatment area 12 (such as shown in FIG. 1) via the stimulator 40 to identify the presence of one or more nerve bundles or fibers or to test the function of a previously identified nerve. In some embodiments, the user/surgeon may administer the stimulus via the electrode 48 on the stimulator 40, for example, upon depressing a button or foot pedal 44 type input device or by tapping a soft-key on the user input display. The electrical stimulus 42 may, for example, be a periodic stimulus that includes a plurality of sequential discrete pulses (e.g., a step pulse) provided at a frequency of less than about 20 Hz, or between about 2 Hz and about 16 Hz. Each pulse may have a pulse width within the range of about 50 μs to about 400 μs. In other examples, each discrete pulse may have a pulse width within the range of about 50 μs to about 200 μs, or within the range of about 75 μs to about 125 μs. Additionally, in some embodiments, the current amplitude of each pulse may be independently controllable.

If a nerve extends within a predetermined distance of the electrode 48, the electrical stimulus 42 may cause the nerve to depolarize, resulting in a mechanical twitch of a muscle that is innervated by the nerve (i.e., an artificially-induced mechanical muscle response). As noted above, each NMS 34 may be specially configured to monitor a local mechanical movement of an adjacent muscle group of the subject 14. In response to this sensed movement, each respective mechanical sensor 50 may generate a mechanomyography (MMG) output signal 52 that corresponds to the sensed mechanical movement, force, and/or response of the adjacent muscle. The MMG output signal 52 may be either a digital or analog signal, and the NMS 34 may further include any communication circuitry or local processing circuitry that may be required to transmit the MMG output signal 52 (or a suitable representation thereof) to the host processor 38 via a wired or wireless communications. In some embodiments, the NMS 34 may further include a local alert capability, such as a lighting module or audible alert module that may operate at the direction of the local processing circuitry or local processor 38 to provide a corresponding visual or audible alert upon the detection of an event.

Detection Algorithm

As noted above, the system 10 may include resident software, firmware, or embedded processing routines that are operative to analyze the output from the neuromuscular sensors 34 in an effort to identify muscle responses that were induced by an electrical stimulus 42 applied via the stimulator 40 (i.e., an induced response). More specifically, these techniques/algorithms may attempt to establish with a high degree of confidence, that a detected muscle movement is the result of a nerve being artificially depolarized (i.e., via a stimulus administered by the stimulator probe) and that the detected motion is not simply a subject-intended muscle movement, an environmentally caused movement (e.g., bumping the operating table), or an artifact of another aspect of the procedure (e.g., sequential compression devices or cautery). In varying embodiments, the detection techniques/algorithms may be performed in the analog/time domain, the digital/frequency domain, and/or may employ one or more wavelet analyses in an effort to promptly and accurately characterize any sensed motion. Additional techniques such as response gating, stimulus frequency modulation, artificial intelligence/structured machine learning, and/or ensemble approaches may also be used to make this detection more robust and/or provide a greater degree of confidence in the detection. While different detection techniques may each prove to be sufficiently effective in making this characterization, in many instances, however, detection confidence and detection speed/time are in conflict. The following will summarize analog/time domain detection techniques, digital/frequency detection techniques, and then go into further detail on wavelet-style analyses that have been found to generate more rapid responses for comparable levels of accuracy and at higher degrees of confidence.

Analog/Time Domain Event Detection

In some embodiments, the signal processing algorithms used to recognize an induced response may involve one or more analog detection techniques such as described, for example, in U.S. Pat. No. 8,343,065, issued on Jan. 1, 2013 (the '065 Patent), which is incorporated by reference in its entirety. In the analog techniques, the processor may examine one or more aspects of the MMG output signal 52 in an analog/time domain to determine if the sensed response includes signal attributes that are indicative of a response of the muscle to the stimulus. These analog aspects may include, for example, the time derivative of acceleration or the maximum amplitude of the M-wave/initial response being above a predetermined threshold. While these signal traits often have a high degree of sensitivity, they often deliver a significant number of false positives if viewed in isolation (i.e., a single spike in the waveform could just as easily be caused by a sharp bump of the operating table). As such, to provide a robust determination, multiple consecutive events need to be detected to make a final characterization. That said, in many instances ample muscle settling time must be provided between adjacent events to ensure that sequential muscle contractions do not overlap to introduce constructive or destructive signal interference in the waveform parameters, which are often dependent on absolute magnitudes or rates of change. The requirement for muscle settling time could limit the stimulation frequency to less than about 4 Hz, or even 2 Hz or less.

Digital/Frequency Domain

In a digital context, such as described in US 2015/0051506, filed on Aug. 13, 2013 (the '506 Application), which is incorporated by reference in its entirety, the processor may convert the analog waveform into the frequency domain (e.g., via a discrete fourier transform, or fast fourier transform) and then compare the frequency characteristics of the MMG output signal with the known frequency of the applied stimulation to determine whether the sensed muscle responses and/or "events" were induced by the applied stimulus. While this is a more robust form of detection than simply searching for discrete analog signal characteristics, the fourier transform necessarily requires a certain amount of accumulated data to perform the spectral decomposition. Thus, any performed analysis is necessarily occurring on buffered data and thus is delayed.

Wavelet Analysis

As a third potential manner of detecting artificially induced muscle responses, the system may include software or firmware that performs a wavelet similarity analysis on the incoming signals. The use of wavelet signal analyses presents an improvement over the frequency-domain detection techniques as it operates on real-time data as it is received without the need to convert to the frequency domain via an FFT. Likewise, it provides a more robust characterization than simply examining discrete signal parameters (e.g., magnitude or rate of change) in isolation.

In a wavelet analysis, one or more analog wave patterns may be pre-selected as being reference "mother wavelets" that bare a resemblance to a smoothed MMG event. A filtered analog waveform in the MMG output signal 52 may then be compared, in real time, to each mother wavelet to determine a degree of similarity between the two. If the presence of the mother wavelet is found within the analog signal, then the system may infer that an artificially induced muscular event has occurred. This is a more robust analysis than the analog method described above largely because it considers the entire wave shape rather than instantaneous parameters.

Because the responsiveness of each subject's muscles (and/or muscle groups) may have different dynamic properties, in some embodiments, the system 10 may also search for the presence of different time-scaled variants of the mother wavelet within the analog signal. These variants are generally referred to as "daughter wavelets," and are similar to the mother wavelet except in how compressed or stretched the wave is on the time-axis.

To perform this analysis, the system 10 may first derive a plurality of "daughter wavelets" from each mother wavelet, where the daughter wavelets are each time-scaled versions of their respective mother wavelet. When analyzing an incoming wave, the examined wave may be continuously passed across each daughter wavelet to determine a respective degree of similarity between the incoming signal and each daughter wavelet (i.e., the degree of similarity being expressed in the form of a "convolution coefficient"). The convolution coefficient for each daughter wavelet may then vary with time as the examined wave passes across the daughter wavelet. This analysis may be performed, for example, using a continuous wavelet transform or discrete wavelet transform and may output a 2d matrix 100 of convolution coefficients such as represented via the heat map in FIG. 9. In this figure, the convolution coefficient may be continuously computed for each scaled daughter wave (represented across the Y/Scale axis 102) and may be output continuously over time (represented on the X/Time axis 104). It should be appreciated that other wavelet-based analysis techniques exist (most commonly in the field of digital image compression) and may be used in combination with or instead of continuous or discrete wavelet transforms for the purposes described herein.

Figure 9:
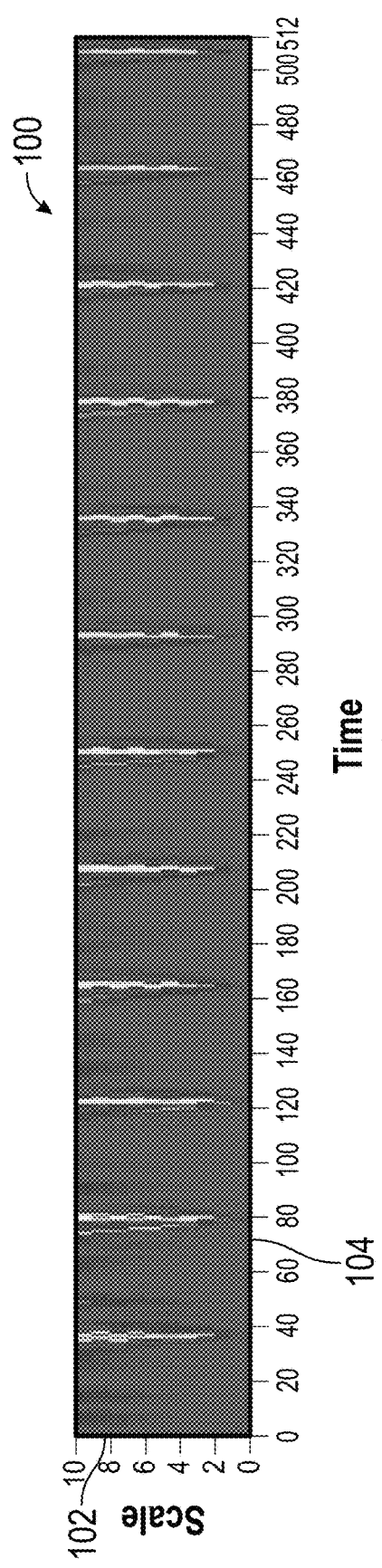
FIG. 9 is a schematic heat map illustrating the magnitude of a convolution coefficient computed for a plurality of different scaled waves (y-axis) across a plurality of different time steps (x-axis).
Figure 10:
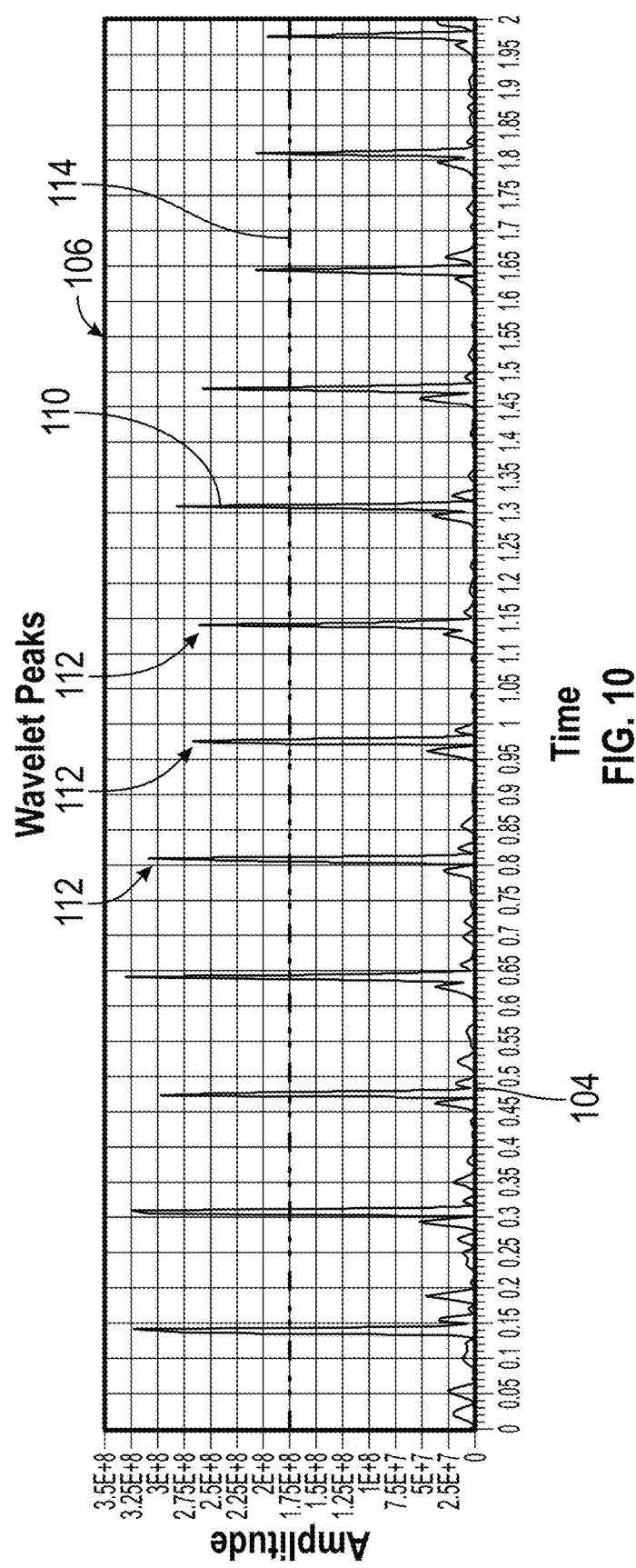
FIG. 10 is a schematic graph of a net convolution coefficient as a function of time, and formed by condensing the heat map of FIG. 9.

The heat map of FIG. 9 may then be consolidated into a more manageable 1-dimensional array 106 by summing the convolution coefficients of each daughter wave across the range of scales into a single net-convolution coefficient 110 (NCC 110) at each timestep, such as generally illustrated in FIG. 10. In some embodiments, each respective convolution coefficient at a time step may be squared prior to summing to ensure that the collection exclusively contains positive values. This is done so that regardless of the orientation of the input signal (whether in phase or out of phase with the wavelet), the output data is always collected as a positive contribution. This resulting 1-dimensional NCC 110 can then provide an indication of the likely temporal locations of the wavelet-like signal within the examined wave in real-time (i.e., with each peak corresponding to a candidate induced neuromuscular event).

As further illustrated in FIG. 10, the NCC may have distinct peaks 112 or spikes in magnitude that may be identified via the processor using a peak finding algorithm. Such a peak finding algorithm may examine the signal for points above a given threshold 114 (typically defined as a percentage of a maximum signal value) that have lower magnitude data points before and after in time. The processor may then process the data from the peak finder by determining whether adjacently identified peaks 112 occur at an expected periodicity. More specifically, in one configuration, the stimulating signal may be administered at a known frequency or periodicity. As used herein, the term periodicity is intended to refer to the spacing in time (i.e., "period") between adjacent peaks and is the inverse of the term "frequency." When examining the temporal identification of the peaks 112 in the NCC 110, the processor may determine a periodicity of the peaks 112 (i.e., by computing the time between adjacent peaks 112), and then compare this to the known periodicity of the stimulus. If the stimulus periodicity and NCC peak periodicity are similar (i.e., within a predefined error tolerance), then the system may conclude that the stimulus 42 is inducing the neuromuscular motion detected by the sensor.

Similar to the analog and frequency techniques described above, requiring an increased number of recorded muscle events/NCC peaks 112 prior to providing an alert would result in improved noise rejection and accuracy, while requiring fewer recorded muscle events/NCC peaks 112 prior to an alert, thus resulting in a faster alert time. In this manner, the wavelet detection techniques provides an ability for an early warning indication upon recognizing only two peaks in the NCC, while it may then provide a more confident alert as subsequent peaks are detected at the known periodicity.

Response Gating

Any of the above-described techniques may be made more robust by further considering only events or muscle activity that occurs within an expected response window following the administration/delivery of the stimulus. Conversely, responses that are "detected" outside of this response window may be aggressively filtered/attenuated or even ignored as not being the result of an applied stimulus (i.e., since no stimulus was administered, it's unlikely that any detected motion was stimulus-induced). In one embodiment, this filtering technique may simply include examining MMG signals for induced muscle response only when the stimulus is being actively applied and effectively turning off detection when the stimulus is not being administered.

In still other embodiments, because the neuromuscular sensors may continue to monitor throughout the duration of the procedure, signal content detected when the stimulus is off may then be used to filter the signal content while the stimulus is being administered. In doing so, background noise may be dynamically detected and filtered out to better isolate portions of the signal that may be representative of an artificially induced muscle response. For example, if there is a repeating 0.5 Hz wave that is detected by the neuromuscular sensor both inside and outside of the expected response window, a signal filter may be trained to remove this signal component from the MMG output signal prior to performing any analysis.

Error Rejection Via Variable Frequency Stimulation

During a surgical procedure, various equipment and interventional processes may act on the patient at various periodic frequencies (e.g., sequential compression devices). In some embodiments, the stimulation frequency may simply be selected to avoid any interference with known intervention frequencies that exist in common practice. In other embodiments, to provide even greater error rejection, the system may stimulate tissue via the probe at a variable stimulation frequency (i.e., a variable periodicity such that the time period between a first and a second provided electrical stimulus is not equal to the time period between the second and a third provided electrical stimulus). This technique may be most easily used in conjunction with a wavelet analysis, where, as shown in FIG. 10, the net-convolution coefficient 110 may generate peaks 112 that would have a varying peak-to-peak period that should directly correspond to the varying period of the administered electrical current.

This variable stim-frequency technique may be particularly applicable to a wavelet detection algorithm because the wavelet algorithm operates in real time on the received signal. In one configuration, the stimulation frequency may be continuously variable such that any two adjacent stim-to-stim periods may be different in length. Such a continuously variable stim-frequency technique is more difficult to implement if using a frequency-domain detection algorithm because the FFT used to decompose the analog signal into the frequency domain requires at least three or four cycles of data before it can provide a reliable frequency decomposition. If the frequency were to be continuously changing, then the FFT may identify a broader range of signal content that may be more difficult to properly characterize.

Dynamic Confidence Determination

It must be noted that each of the above-described detection techniques can yield statistically accurate detection results if provided enough time/data. For example, in an analog context, if 10 or more MMG events were detected in a consecutive sequence, where each event was identified as having a time derivative of acceleration value above a threshold, there is an extremely high likelihood that these 10 sequential events were caused by a corresponding 10 pulses of a stimulation current. Conversely, if only a single event were considered prior to making a determination, there is a much greater likelihood that this candidate "event" could be a false positive, which may have been caused simply by the operating table being bumped with a sufficient force. To this end, requiring more candidate events to confirm an alerted event may provide greater statistical accuracy/confidence in the determination, however it would also require a greater amount of time to reach that determination. This is because each "event" is a discrete contraction of the muscle that is induced by a separate electrical stimulus provided over time.

Figure 11:
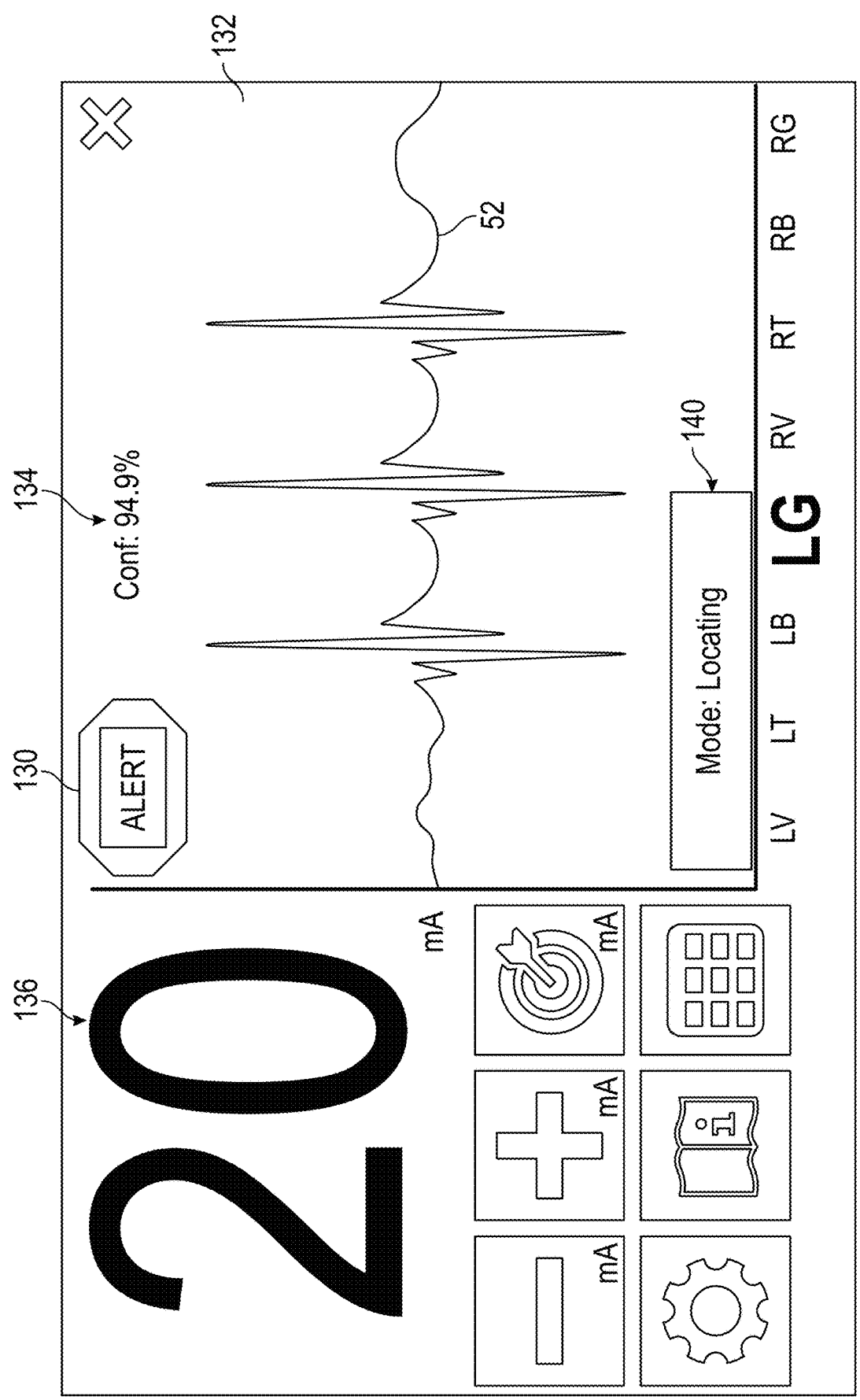
FIG. 11 is a schematic display screen for a neural monitoring system, such as shown in FIG. 1, with the display screen indicating that the system is in a nerve locating mode, though has high confidence that a nerve has been detected via a 20 mA stimulation current.

In view of the tradeoff between speed and confidence, in one configuration, the processor 28 may be configured to indicate or provide an alert 130 if a possible MMG event is detected, such as shown in the display screen 132 in FIG. 11, while also providing an indication of a statistical confidence 134 that the event is, in fact, a stimulus-induced muscle response. As further illustrated via the display screen 132 in FIG. 11, the processor 28 is further configured to provide an indication 136 of the magnitude of the electrical current administered via the electrode 48, as well as a raw or filtered analog trace of the MMG output signal 52. For example, referring to the wavelet discussion, above, if a single peak 112 is detected in the computed net-convolution coefficient 110, the system may provide an indication that an event is detected, however, it may also indicate that this detection has a comparatively low level of confidence because it is a singular event and therefore there is no peak-to-peak period yet. Upon detection of second consecutive event, the indication of the induced muscle response (e.g., an alert to a user) may persist, though the provided degree of confidence may increase. This is because now two candidate events have been detected, and further because now there is a peak-to-peak period that can be compared to the stimulation period. Upon detection of, for example, a third or fourth consecutive peak, the indicated degree of confidence may increase further (both because detecting three or four events provides more confidence than, for example, two or three events, but also because there is additional period-data, and at four cycles of data, the FFT may be more accurately computed and the output of the FFT may serve to further confirm the output of the wavelet analysis). As such, with more identified candidate events and elapsed time, the system has more and more data from which to make a more confident determination.

As demonstrated from this example, the processor may utilize different detection techniques in combination and/or may utilize varying detection criteria for any given technique to provide an overall confidence determination. If represented quantitatively, such as shown in FIG. 11, a statistical measure of confidence 134 may be a function to the sensitivity, specificity, positive predictive value (PPV), and/or negative predictive value (NPV) of the event determination based on the amount and nature of the information that has been received. In a non-limiting example, the statistical confidence reading may be the root-mean-squared (RMS) of the empirically determined PPV and NPV for the detection technique when trained against known data. As more data is received, this confidence determination may be refined upward (using new event info that supports the determination) or downward (based on identified signal parameters that are in conflict with a true event). In one embodiment, the confidence determination may be visualized on the display as a single column bar chart, a gauge, a dial, or any other qualitative or quantitative indication of the relative degree of confidence in the predictive value of the alert 130.

Providing a early indication of a possible event, along with a statistical indication of confidence in that determination may enable a faster time to detection and ultimately provide the surgeon with increased understanding and trust in the alert. While in some instances, detection speed may simply be a matter of convenience, in other instances it can directly impact usability and/or system dynamics. For example, if the system is serving as an input to a robotic system, an early indication of the presence of a nerve (even if associated with a low statistical confidence) may enable the control dynamics to more rapidly begin implementing prophylactic measures to slow or halt the robot's motion.

Confidence Using Wavelet Techniques

In one embodiment, the processor 28 of the neural monitoring system 10 may alert a user to the occurrence (or lack thereof) of an artificially induced neuromuscular response if one or more peaks 112 are identified in a net-convolution coefficient 110 (NCC), such as described above. Using an understanding of the system's capabilities via empirical data, the system may also be able to compute and output an indication of the confidence 134 of the alert 130 based on the number and periodicity of the identified NCC peaks 112.

To demonstrate this confidence determination, the data in the following table was obtained via controlled bench testing using a wavelet-style analysis and a 16 Hz stimulation signal. It must be noted that this data is illustrative based on preliminary testing and should not be relied upon as demonstrating any capabilities of a commercially available system or as the basis for medical decision making. This data demonstrates that a greater amount of confirmatory information serves to increase the positive predictive value (i.e., more data reduces the incidence of false positives), though that the system (in this test) is not prone to false negatives.

|  | 2 peaks | 3 peaks | 4 peaks |
| --- | --- | --- | --- |
| Sensitivity | 100% | 100% | 100% |
| Specificity | 44.2% | 88.4% | 99.6% |
| PPV | 64.2% | 89.6% | 99.6% |
| NPV | 100% | 100% | 100% |
| RMS (PPV, NPV) | 84.0% | 94.9% | 99.8% |

When using a wavelet analysis, however the NCC 110 is being computed in real-time (or near-real time), and peaks 112 are identified on a rolling basis. While it is clear that a 4-peak detection provides the maximum confidence and highest rate of true positives, every identification of 4 peaks necessarily begins as the observation of two peaks, followed by the observation of three peaks—thus confidence in the alert grows as successive peaks are observed. In this example, with an indication of the alert, the system may also indicate the determined confidence (e.g., PPV or RMS(PPV, NPV)) to the user.

Use Cases

Nerve Detection/Avoidance—Exploratory

In a first embodiment, the present system may be used in an exploratory or nerve-locating manner to detect the presence of nerves within an intracorporeal portion of a subject. Such a use may, for example, include making a lateral-access approach to the spine prior to dilating and/or retracting tissue. In such a use, rapid detection time may aid a surgeon in more fluidly navigating this intracorporeal space while receiving continual updates on the existence of nerves in the local area. Conversely, it may avoid a situation where the surgeon must advance a tool/probe, and then wait for the system to register a response before knowing whether it is safe to advance further.

In one embodiment, during such an exploratory mode of operation, the system may transmit an electrical stimulus via an electrode 48 provided on a distal end portion of an elongate instrument/probe 40 as the probe navigates the intracorporeal treatment area. In one configuration, for this free-space type of detection, the current of the stimulus may be between about 15 mA and about 25 mA, which should be a large enough current to depolarize any nerve within about 15-20 mm of the electrode. Using a wavelet detection approach, together with a dynamic confidence reading, the system may provide an indication of a muscle event 130 after only a single peak is recognized in the net-convolution coefficient. As more data is received, including a second peak, a third peak, a fourth peak, etc. the displayed confidence 134 of the event detection may increase on the display (e.g., numerically and/or graphically via charts). Such a confidence indication may inform the surgeon how likely it is that the alert is a true positive (i.e., that the alert is indicative of an artificially induced muscle response, and not simply a false positive). The provided confidence indication 134 may be further associated with color changes on the display, or changes in the tone of audible alerts that are played. Further, in the display screen, the system may indicate that the system is in a "locating" mode (at 140) which may broadly inform the surgeon that the system is operating simply to detect whether the stimulator 40 is approaching a previously unidentified nerve.

In a robotic surgery context, this low-confidence initial detection may prove very useful to the control systems, which must account for system dynamics in tool movement. Thus, in one configuration, even a low confidence detected event may impose limits on the robot as far as maximum probe tip travel speed, limits on angular movement, or limits on tool actuation.

Nerve Detection/Avoidance—Threshold Determination

Figure 12:
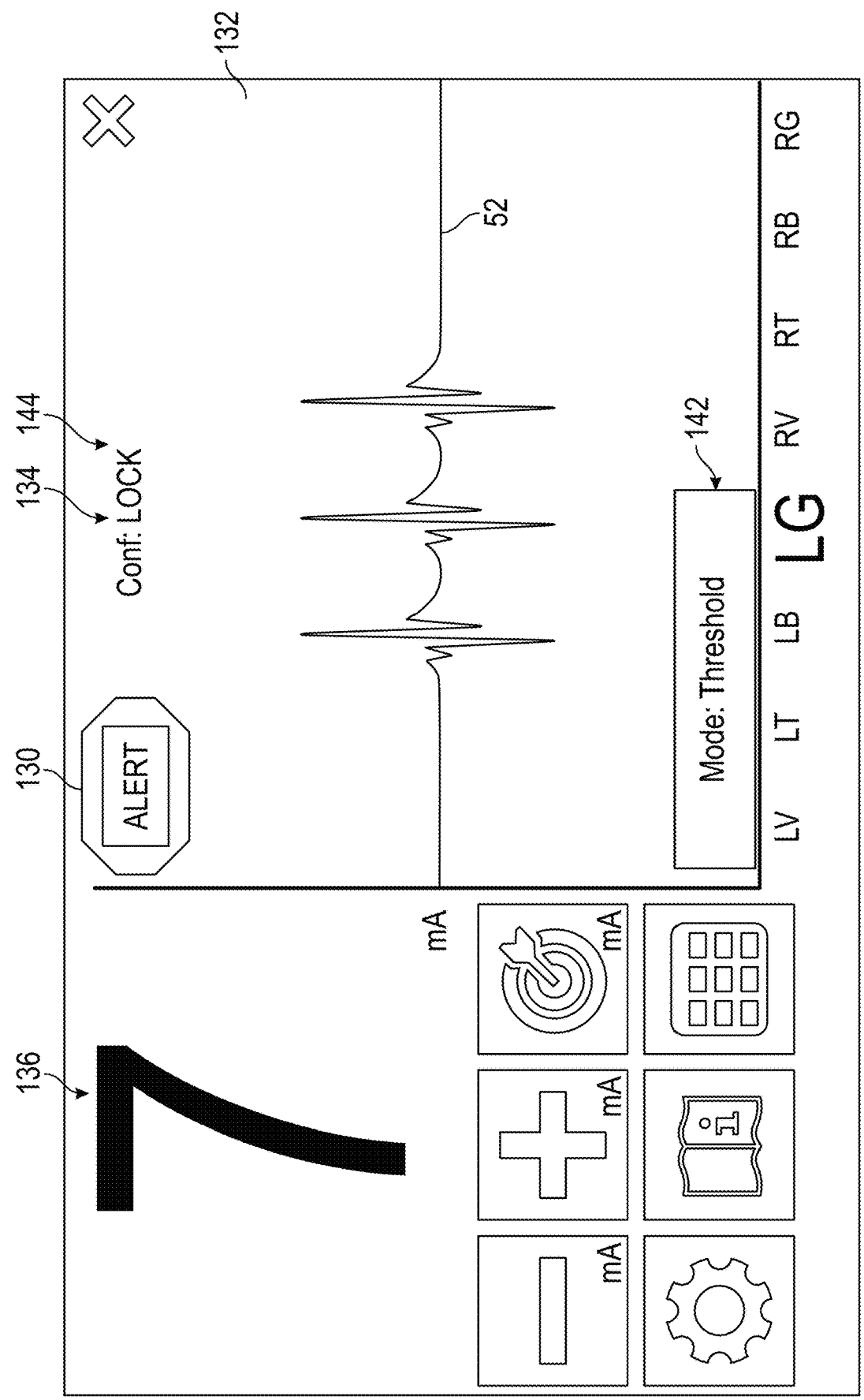
FIG. 12 is a schematic display screen for a neural monitoring system, such as shown in FIG. 1, with the display screen indicating that the system is in a threshold determining mode though has achieved a high-confidence "lock."

Once a neuromuscular response is detected with sufficient confidence (e.g., four successive peaks observed in the NCC 110), the system may then attempt to determine the minimum current that is required to induce a perceivable muscle response. This value has some clinical relevance as it is strongly correlated with the distance between the electrode and the nerve. During this threshold determination, the system may utilize a "confidence lock" feature to effectively lock on to a repeating muscle response and allow the magnitude of the stim current to vary from pulse-to-pulse. In some embodiments, when attempting to determine the minimum depolarization current for an identified nerve, the system may indicate, via the display 132, that the mode of operation is now threshold-finding 142 and may further provide an indication that the confidence is in a high confidence "lock" state 144, such as illustrated in FIG. 12. Once in this locked state, the processor 28 may disregard 1-pulse dropouts in the muscle response signal from affecting the detection confidence—provided those drop-outs coincide with a reduction in stim current (suggesting the stim current may have fallen below a nerve-depolarization threshold) and/or if they can be remedied by an immediate increase in stimulation current.

As an example of this technique, a surgeon may make an approach with a stimulated probe toward the spine with the system in the nerve-locating mode (as indicated at 140 in FIG. 11). Once a neuromuscular response is detected with sufficient confidence, the processor 28 may transition to a threshold-determining mode (at 142 in FIG. 12) and begin ramping down the magnitude of the current until it can be observed that a particular stimulus pulse fails to result in an observed or threshold peak 112 in the NCC 110. Due to the decreasing magnitude of the stimulus current, the processor 28 may assume that the lack of the response is more attributable to an insufficient current to depolarize the nerve, and not because the nerve (which confidently existed a moment ago), suddenly disappeared (or significantly moved relative to the probe). To confirm this assumption, the processor 28 may then increase the current magnitude to a prior (or simply a higher) level and examine if the peak 112 returns. If it does, the system may remain in the confidence lock state, while further concluding that the depolarization threshold current lies between the prior two current levels, which may then be indicated to the surgeon.

If the probe continues advancing toward (or away) the nerve, the system may attempt to follow this depolarization threshold by modulating the current in a similar scheme while maintaining the confidence lock so long as any drop out can be remedied by an increase in current. If the current magnitude returns to its original exploratory level (e.g., 15 mA to 25 mA), and multiple no-responses are observed, then the system may return back to a high confidence no-nerve state. Through this process, a decreasing depolarization threshold would indicate that the motion of the probe is bringing the electrode closer to the nerve, whereas an increasing depolarization threshold would indicate that the electrode is moving away from the nerve. By using the wavelet analysis technique in this manner, the processor may track the depolarization threshold on only a one pulse/cycle lag as opposed to, for example, an FFT approach that requires 3-4 cycles/pulses of data for each analysis.

Nerve Health Diagnostics

In one embodiment, present system may be used to determine the health, or change in health of a nerve. More specifically, as nerves become compressed within a neural foramen, they lose their ability to transmit a clean neurological impulse to the muscle that they innervate. Assuming that the nerve has not been permanently damaged through prolonged compression, decompressing the nerve by removing the stenosis or impinging tissue can result in an almost immediate improvement in nerve function. In this manner, the present system may be used to determine both the extent of a nerve compression, as well as to serve as an intraoperative diagnostic tool to identify the point at which the nerve is sufficiently decompressed (which may provide an indication to conclude the procedure).

To perform the nerve health diagnostics, it is preferable to directly stimulate the nerve or nerve root, via contact between the electrode and the nerve, both before and after the decompression to assess changes in the nerve/muscle response. To accomplish this direct stimulation, in one configuration, a stimulator probe such as shown in FIG. 3 or FIG. 7 may be inserted into the vertebral foramen above or below the posterior lamina and the electrode 48 may be brought into contact with the nerve (i.e., contacting the nerve on the anterior side of the lamina). The thin/flat geometry of the above-described stimulator tip provides a surgeon with the ability to make this direct contact even if an impingement or stenosis provides minimal space that would not accommodate more traditional (e.g., ball tip) probes without some degree of pre-decompression first.

Once in contact with the nerve, the system may attempt to determine the minimum amount of current that is required to sufficiently depolarize the nerve and induce a perceivable muscle response. In the case of healthy nerves, the minimum required current to induce a muscle response may be between about 1 mA and about 6 mA, or more preferably between about 1 mA and about 3 mA. Conversely, some compressed nerves may require between about 15 mA and about 30 mA to elicit the same threshold response. By testing the minimum required current before, during, and after the decompression, the surgeon may better understand the initial health and/or functionality of the nerve, and whether further decompression or exploratory efforts may be required to provide a successful outcome.

The present system may utilize various techniques to determine the minimum current in the shortest amount of time. For example, in one configuration, the system may linearly ramp the current up from 1 mA to a point where a muscle response is detected. In another configuration, the system may use algorithmic targeting techniques to identify the minimum required current in the fewest number of iterative steps. Such a targeting technique may involve identifying a total working current range and then testing a current value at the center of the working range. This test should result in one of the two created sub-ranges being bounded by a current value that does not induce a muscle response on the low end, and a current value that does induce a muscle response on the higher end of the sub-range (i.e., in binary terms, this sub range could be represented as a "0-1" range—as opposed to a "0-0" range where neither endpoint sees a muscle response or "1-1" range where both endpoints see a response). The system may then test at the center point of the identified 0-1 subrange to then identify a 0-1 sub-subrange within the previously identified 0-1 sub-range. This process may repeat until a suitable sub-range resolution is achieved that contains the actual threshold. If the initial starting range was 0-20 mA, then it would only take five tests to identify the minimum current threshold with sub-1 mA resolution ($20/(2^5)=0.625$ mA resolution).

While it is certainly possible to perform each test in this sequence of five tests to a full confidence (i.e., where each test requires a sequence of consecutive simulations/muscle responses), in some embodiments, the process may be further sped up using a wavelet approach that takes into account the confidence of the determination. For example, the first test (e.g., at 20 mA) may have a lower required confidence threshold to determine an event than the later tests.

Alternatively, the system may utilize a similar "confidence lock" scheme as described above to home in on the threshold while altering the current magnitude between each successive pulse (i.e., once a lock is established). For example, the system may begin at a high current (e.g., 20 mA) in an attempt to achieve a response and high-confidence lock. Once locked in this high-confidence mode via a plurality of successive responses having a periodicity that approximates or is about equal to a periodicity of the stimulus, then each successive test may only require a single stimulus pulse. If, by dropping the current, a response is not recorded, and then the current is increased on the next stimulus and the muscle response returns at the expected time, then the high confidence lock may be maintained. As an example, if the threshold for a high-confidence lock is three consecutive events occurring at a periodicity that is about equal to a periodicity of the stimulus, then the stim sequence to home in on a 6.5 mA threshold may proceed as set forth in the table below:

| Pulse No. | Current | NCC Peak Detected? | Comments |
|---|---|---|---|
| 1 | 20 mA | Yes | Establishes High |
| 2 | 20 mA | Yes | Confidence Lock |
| 3 | 20 mA | Yes | |
| 4 | 10 mA | Yes | Bounded Range: 0-10 mA |
| 5 | 5 mA | No | Bounded Range: 5-10 mA |
| 6 | 7.5 mA | Yes | Bounded Range: 5-7.5 mA Negates missed peak on pulse 5 |
| 7 | 6.125 mA | No | Bounded Range: 6.125-7.5 mA |
| 8 | 6.813 mA | Yes | Bounded Range: 6.125-6.813 mA (sub-1 mA accuracy) |

In this example, the first three 20 mA stim pulses are used to establish the high-confidence lock, and then the subsequent 5 pulses are each singular pulses, with the step up from 5.0 mA to 7.5 mA in pulse #6 and the step up from 6.125 mA to 6.813 mA in pulse #8 (and return of the NCC peak in each instance) negating any drop in confidence from the lack of response at 5.0 and 6.125 mA, respectively. If stimulated at an 8 Hz stim frequency, this total detection scheme would take 1 second—as compared with other detection techniques that may require 20 or more stim pulses, and multiple seconds of detection time, to arrive at the same detection resolution (potentially at even slower stim frequencies).

Robotic System with Rapid Nerve Detection

Figure 13:
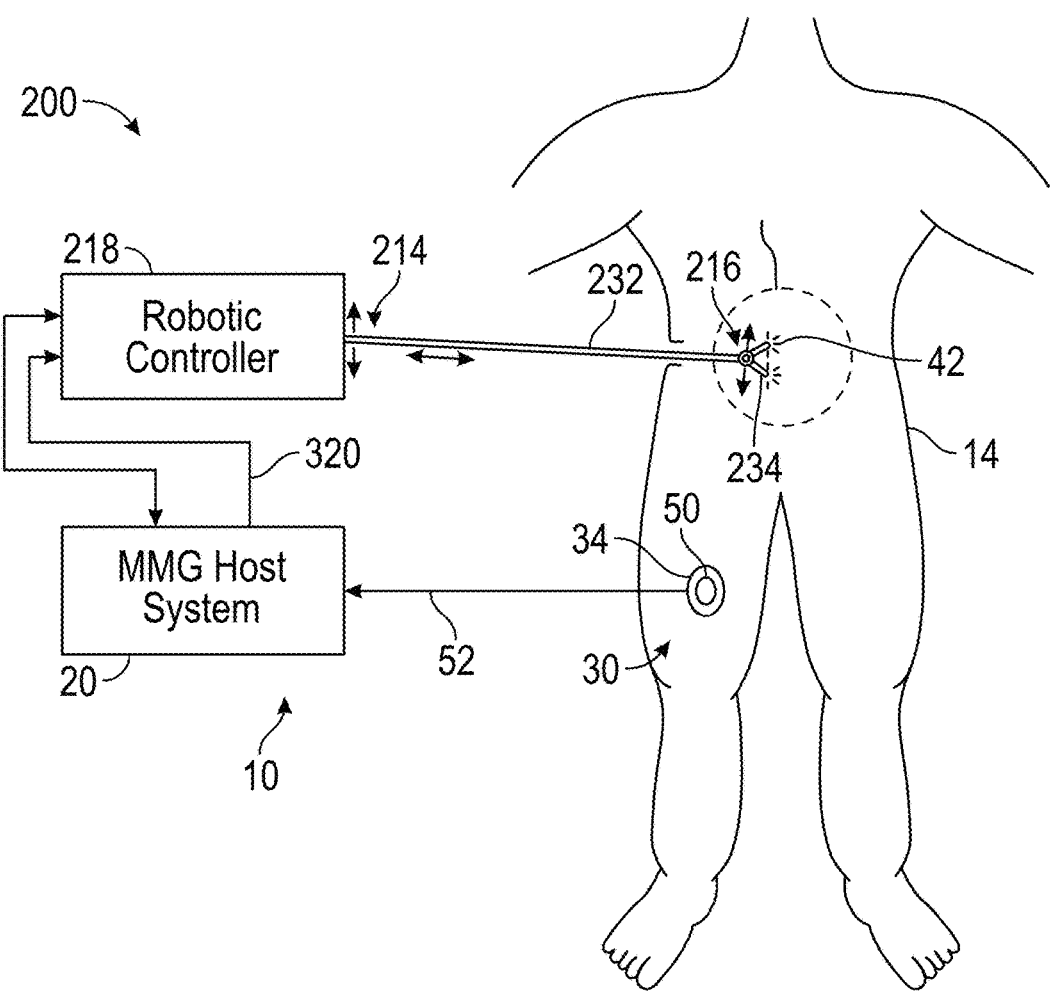
FIG. 13 is a schematic illustration of a robotic surgical system with mechanomyographic feedback being used in conjunction with a human subject.

FIG. 13 schematically illustrates a robotic surgical system 200 for performing a surgical procedure within the body of a subject 14. As illustrated, the robotic surgical system 200 includes an elongate surgical instrument 212 having a proximal end portion 214 and a distal end portion 216, a robotic controller 218 configured to control the motion of the distal end portion 216 of the surgical instrument 212, and a neural monitoring system 10 in communication with the robotic controller 218. As discussed above, the neural monitoring system 10 may include a sensing device 30 that includes at least one neuromuscular sensor (NMS) 34 that is coupled with the carrier material 32 and is operative to monitor a muscular response of the subject 14. each NMS 34 may comprise a mechanical sensor 50 that is operative to monitor the relative movement of the muscle that the NMS 34 is most closely coupled with.

During a surgical procedure, the surgical instrument 212 may extend through an opening in the body of the subject 14, with the distal end portion 216 disposed within the body of the subject 14, and the proximal end portion 214 disposed outside of the body of the subject 14. In one configuration, the surgical instrument 212 may generally be defined by a rigid elongate body 232, such that movement of the proximal end portion 214 of the instrument 212 may result in a predictable movement of the distal end portion 216 of the instrument 212.

The surgical instrument 212 may further include an end effector 234 disposed at the distal end portion 216. The end effector 234 may be responsible for performing one or more cutting, grasping, cauterizing, or ablating functions, and may be selectively actuatable in at least one degree of freedom (i.e. a movable degree of freedom, such as rotation, or an electrical degree of freedom, such as selectively delivering ablative energy). Additionally, the end effector 234 may be configured to selectively rotate and/or articulate about the distal end portion 216 of the surgical instrument 212 to enable a greater range of motion/dexterity during a procedure.

In one embodiment, such as generally illustrated in FIG. 13, the end effector 234 may be configured to resemble forceps, and may have one or more controllably movable jaws adapted to articulate about a hinged joint. The selective articulation of the one or more jaws may be enabled, for example, by cables or pull wires extending to the robotic controller through the rigid elongate body 232 of the instrument 212.

Figure 14:
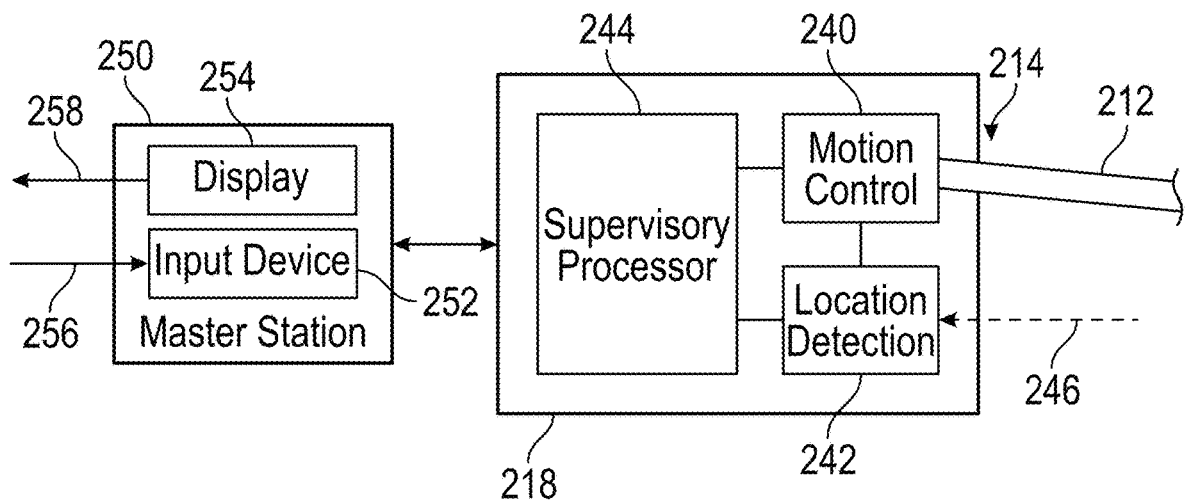
FIG. 14 is a schematic diagram of a robotic controller such as may be used with the robotic surgical system of FIG. 13.

The robotic controller 218 may be responsible for controllably performing a minimally invasive surgical procedure within the body of the subject 14 by controllably manipulating the proximal end 214 of the surgical instrument 212 in a manner that results in a controlled motion of the distal end portion 216. As generally illustrated in FIG. 14, in one configuration, the robotic controller 218 may include a motion controller 240, a location detection module 242 and a supervisory processor 244. The motion controller 240 may include a plurality of motors, linear actuators, or other such components that may be required to manipulate the proximal end 214 of the surgical instrument 212 in six or more degrees of freedom. (e.g., three degrees of translation, three degrees of rotation, and/or one or more degrees of actuation). Additionally, the motion controller 240 may include one or more processors or digital computers and/or power electronics that may be required to convert a received motion command into a physical actuation of a motor or actuator.

The location detection module 242 may include one or more digital computers or processing devices that may be configured to determine the position/motion of the distal end portion 216 of the surgical instrument 212, such as relative to one or more external reference frames. In one configuration, the location detection module 242 may monitor the behavior of the motion controller 240 to determine the motion of the distal end portion 216 using kinematic relationships of the surgical instrument 212. In another configuration, the location detection module 242 may receive a location signal 246 from an external, positioning system (not shown), which may resolve the position of the distal end portion 216 of the surgical instrument 212 using, for example, ultrasound energy, magnetic energy, or electromagnetic energy that may be propagated through the subject 14.

The supervisory processor 244 may be embodied as one or more digital computers or data processing devices, each having one or more microprocessors or central processing units (CPU), flash memory, random access memory (RAM), electrically-erasable programmable read only memory (EEPROM), a high-speed clock, analog-to-digital (A/D) circuitry, digital-to-analog (D/A) circuitry, input/output (I/O) circuitry, power electronics/transformers, and/or signal conditioning and buffering electronics. The individual control routines/systems resident in the supervisory processor 244 or readily accessible thereby may be stored in flash or other suitable tangible memory location and/or memory device, and automatically executed by associated hardware components of the processor 244 to provide the respective control functionality. In one embodiment, the supervisory processor 244 may provide the motion controller 240 with actuation commands in a closed loop manner using the positional feedback provided by the location detection module 242. The supervisory processor 244 may perform any combination of feedforward, feedback, and/or predictive control schemes to accurately control the motion and/or actuation of the distal end portion 216 of the surgical instrument 212.

Additionally, the robotic controller 218 may be in communication with a master station 250 that includes a user input device 252 and a user feedback device such as a display 254. The user input device 252 may receive an input 256 from a user that corresponds to an intended movement of the distal end portion 216 of the surgical instrument 212. The master station 250 may then provide a motion command to the robotic controller 218 that corresponds to the received input 256. Similarly, the master station 250 may receive visual information 258 from the robotic controller and convey it to the user via the display 254.

While FIG. 14 provides one embodiment of a robotic controller 218, other embodiments, configurations, and or control schemes may similarly be used to manipulate the surgical instrument 212 in a manner that results in a controlled, and intended motion of the distal end portion 216. While the robotic controller 218 and surgical instrument 212 described above are generally of the kind used for robotic laparoscopy, such description is made for illustrative purposes and should not be limiting. Other minimally invasive surgical systems that employ a robotic controller 218 to control the motion of the distal end of an elongate surgical instrument may include, for example, robotic catheter systems and/or robotic endoscopic systems.

Referring again to FIG. 13, the robotic surgical system 200 includes a neural monitoring system 10 in communication with the robotic controller 218. The neural monitoring system 10 may provide the robotic controller 218 with an awareness of nerves that may be adjacent to the distal end portion 216 of the surgical instrument 212. In this manner, the robotic system 200 may avoid manipulating tissue (either through translational motion or actuation of an end effector 234) that may jeopardize neural integrity.

During a surgical procedure, the elongate surgical instrument 212 may emit a stimulus 42 within the intracorporeal treatment area 12 of the subject 14 similar to the simulator 40 described above. The stimulus 42 may be, for example, an electrical stimulus, though may alternatively be a thermal, chemical, ultrasonic, or infrared stimulus.

With continued reference to FIG. 13, if the neural monitoring system 10 detects an induced muscle response via the NMS 34, it may then provide a control signal 320 to the robotic controller 218. The control signal 320 may include an indication that an induced muscle response was detected. In some embodiments, this indication may include one or more of: a binary alert/signal (i.e., a nerve either is detected or it is not detected); an indication of the confidence of a detection (i.e., using one or more of the techniques described above), an indication of proximity between the distal end portion 216 of the surgical instrument 212 and a depolarized nerve, and/or an indication of a minimum current required to induced a muscle response.

Upon receipt of a control signal 320, the robotic controller 218 may artificially constrain the motion of the distal end portion 216 of the surgical instrument 212 to avoid inadvertent contact with a proximate nerve 340. For example, in one configuration, the robotic controller 218 may be configured to prevent all motion of the distal end portion 216 of the surgical instrument 212 in response to the received control signal 320. As such, if the distal end portion 216 was in motion, the received control signal 320 may cause the controller 218 to halt such motion and await a further command from the user. Additionally, the robotic controller 218 may be configured to limit or prevent actuation of an end effector 234 upon receipt of the control signal 320.

Conversely, in certain therapeutic procedures, the robotic controller 218 may be configured to actuate the end effector 234 upon receipt of the control signal 320 (e.g., selectively deliver ablative energy to tissue proximate to the nerve).

Figure 15:
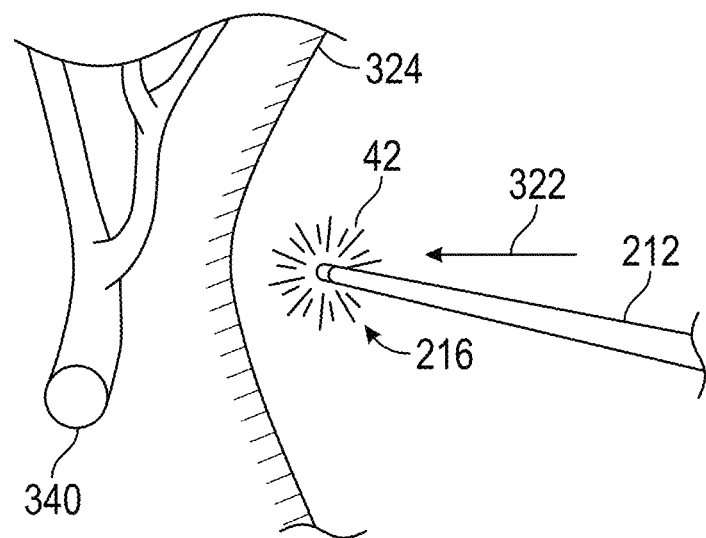
FIG. 15 is a schematic view of a distal end portion of an elongate surgical instrument moving with respect to a nerve of a subject.

In another configuration, such as schematically illustrated in FIG. 15, upon receipt of the control signal 320, the robotic controller may note the direction 322 of the motion of the surgical instrument 212, and may limit further instrument motion in that direction 322 (or directions with a component vector substantially aligned with the direction 322 of motion).

Figure 16:
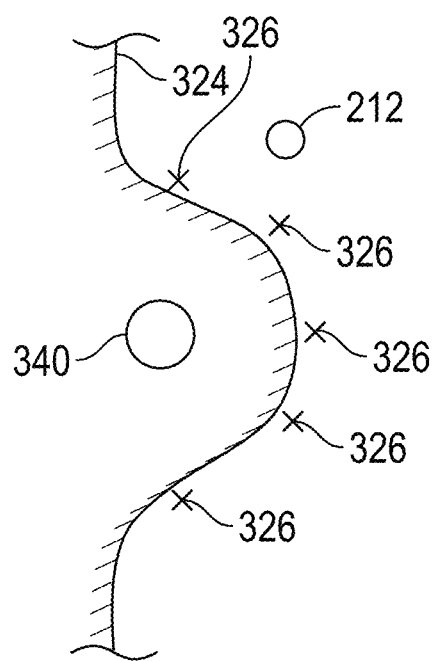
FIG. 16 is a schematic cross-sectional view of FIG. 15, with a virtual barrier being erected about the nerve.

In still another configuration, the robotic controller 218 may construct a virtual barrier 324 based on the direction of motion of the surgical instrument 212, and the location 326 of the instrument 212 when the control signal 320 was received. The virtual barrier 324 may be maintained in an associated memory of the robotic controller 18, and may limit the allowed range of motion of the surgical instrument 212, such that the surgical instrument 212 is artificially restricted from crossing the virtual barrier 324. As generally illustrated in FIG. 16, as the surgical instrument 212 moves, the virtual barrier 324 may be refined according to the receipt of successive control signals 320/locations 326.

Once a nerve is detected, the robotic controller 218 may be configured to vary the permitted speed of the distal end portion 216 of the surgical instrument 212 as a function of the indicated proximity between the real-time location of the instrument 212, the minimum current required to induced a muscular response, and/or the determined confidence of the detection. As such, the instrument 212 may be allowed to move more quickly and/or at a higher rate of speed when it is farther from the nerve. Similarly, by understanding the confidence of a detection, the robotic controller 218 may effectively have an early warning or advanced notice that a confirmed detection may be incoming. In this manner, maximum permitted tip speed may decrease as the confidence of the detection increases. Once a high confidence lock is established (e.g., 4 or more consecutive induced muscle responses have been detected), the maximum permitted tip speed may vary as a function of stimulus magnitude and/or the magnitude of the detected response.

Similarly, if a induced muscle event is detected (i.e., even if it is a low confidence detection), the robotic controller 218 may limit or prevent the actuation of any end effector that may compromise nerve integrity until the alert is cleared. In some embodiments, the surgeon may be provided with the ability to override such a tool restriction, though not until the surgeon is fully alerted of the risk.

If the presence of a proximate nerve is detected (via an induced muscle response), and/or if an action is performed by the robotic controller 218 to adjust or limit the allowed motion of the surgical instrument 212, the robotic controller 218 may likewise transmit an alert (i.e., a visual alert or an auditory alert) to the user via the master station 250.

Using the system described above, robotic, minimally invasive surgery may be performed in a manner that may allow a surgeon to be aware of nerves/nerve roots that may lie within the treatment area. This is important because neural tissue may often be visually indistinguishable from surrounding tissue, thus traditional visual methods of guidance and control may be ineffective. In this manner, using the above-described system, care may be taken to avoid manipulating neural tissue (either intentionally or inadvertently) in a manner that may injure one or more nerves and/or result in long-term paralysis. Said another way, the described system may allow the user and/or robotic controller to "see" the nerves within the treatment area using a non-visual and/or indirect sensing means. Once their presence is identified, appropriate care may be taken to avoid inadvertent or unintended contact with them.

"A," "an," "the," "at least one," and "one or more" are used interchangeably to indicate that at least one of the item is present; a plurality of such items may be present unless the context clearly indicates otherwise. All numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; about or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range. Each value within a range and the endpoints of a range are hereby all disclosed as separate embodiment.

The following clauses present various additional embodiments of the present technology and are intended to be read in light of the preceding disclosure.

Clause 1. A selectively electrifiable nerve stimulator for applying an electrical stimulus to a nerve or nerve root during a surgical procedure, the nerve stimulator comprising:
 an elongate body having a distal end portion that includes a stimulator tip, a proximal end portion that includes a handle or handle connector, and a body portion between the proximal end portion and the distal end portion;
 wherein the elongate body comprises an electrically conductive metallic core and an electrically insulating layer surrounding the electrically conductive metallic core to form an exterior surface of the elongate body, the electrically insulating layer extending between the stimulator tip and the handle or handle connector such that at least a portion of the stimulator tip remains uncovered by the insulating material to form an electrode; and
 wherein the elongate body extends along a central body axis and the stimulator tip including the electrode is pitched away from the central body axis by an angle of between about 30 degrees and about 60 degrees.

Clause 2. The nerve stimulator of clause 1, wherein the elongate body, between the distal end portion and the proximal end portion includes a tapered cross-sectional profile that transitions from a first diameter at a first location near the proximal end portion of about 1.8 mm to about 2.2 mm to a second diameter at a second near the distal end portion of about 0.7 mm to about 0.9 mm.

Clause 3. The nerve stimulator of clause 2, wherein the first location is spaced from the second location by at least about 75 mm.

Clause 4. The nerve stimulator of any of clauses 1-3, wherein the electrically insulating layer comprises a parylene coating.

Clause 5. The nerve stimulator of any of clauses 1-3, wherein the electrically insulating layer comprises a polymer including at least one of a polyvinylidene fluoride (PVDF), a polyether block amide (PEBA), a high-density polyethylene (HDPE), a cross-linked acrylated olefin, a polytetrafluoroethylene (PTFE), a fluorinated ethylene propylene (FEP), or a polyethylene terephthalate (PET).

Clause 6. The nerve stimulator of any of clauses 1-5, wherein the distal end portion further includes a neck portion, the neck portion being located between the proximal end portion and the stimulator tip,
 wherein the neck portion is pitched away from the central body axis by an angle of between about 10 degrees and about 25 degrees, and wherein the stimulator tip is pitched in the same plane as the pitch of the neck portion to forms an angle with the neck portion of between about 100 degrees and about 140 degrees.

Clause 7. The nerve stimulator of any of clauses 1-6, wherein the electrode has a total surface area of between about 10 mm$^2$ and about 20 mm$^2$.

Clause 8. The nerve stimulator of any of clauses 1-7, wherein the stimulator tip has a thickness of between about 0.4 mm and about 0.8 mm, the thickness being measured in the center of the electrode and in the same plane as the pitch of the stimulator tip relative to the central body axis.

Clause 9. The nerve stimulator of clause 8, wherein the stimulator tip has a width, measured orthogonally to the thickness, and wherein the a ratio of the width-to-thickness is between about 3.5:1 and about 4.5:1.

Clause 10. A stimulator for providing a stimulus to intracorporeal tissue during a medical procedure, the stimulator comprising:
 an elongate body with a handle and/or handle connector at a proximal end portion and a stimulator tip at a distal end portion, the handle connector and stimulator tip being electrically conductive and in electrical communication with each other, and the exterior surface of the body between the handle connector and the stimulator tip being non-conductive;
 an electrode disposed on the stimulator tip and being selectively electrifiable to provide a stimulus to the intracorporeal tissue; and
 wherein the elongate body extends along a central body axis and the stimulator tip including the electrode is pitched away from the central body axis by an angle of between about 30 degrees and about 60 degrees Clause 11. The stimulator of clause 10, wherein at least a portion of the body has a tapered cross-sectional profile to provide increased feel and tactile response through nerve-dense regions and around bony anatomy.

Clause 12. The nerve stimulator of clause 11, wherein the tapered cross-sectional profile transitions from a first diameter at a first location near the proximal end portion of about 1.8 mm to about 2.2 mm to a second diameter at a second near the distal end portion of about 0.7 mm to about 0.9 mm.

Clause 13. The nerve stimulator of clause 12, wherein the first location is spaced from the second location by at least about 75 mm.

Clause 14. The nerve stimulator of any of clauses 10-13, wherein the distal end portion further includes a neck portion, the neck portion being located between the proximal end portion and the stimulator tip, wherein the neck portion is pitched away from the central body axis by an angle of between about 10 degrees and about 25 degrees, and wherein the stimulator tip is pitched in the same plane as the pitch of the neck portion to forms an angle with the neck portion of between about 100 degrees and about 140 degrees.

Clause 15. The nerve stimulator of any of clauses 10-14, wherein the electrode has a total surface area of between about 10 mm$^2$ and about 20 mm$^2$.

Clause 16. The nerve stimulator of any of clauses 10-15, wherein the stimulator tip has a thickness of between about 0.4 mm and about 0.8 mm, the thickness being measured in the center of the electrode and in the same plane as the pitch of the stimulator tip relative to the central body axis.

Clause 17. The nerve stimulator of any of clause 16, wherein the stimulator tip has a width, measured orthogonally to the thickness, and wherein the a ratio of the width-to-thickness is between about 3.5:1 and about 4.5:1.

Clause 21. An intraoperative neural monitoring system for use during a surgical procedure, the system comprising:
 a mechanical sensor configured to:
  monitor a physical motion of a muscle of a subject; and
  provide a mechanomyography (MMG) signal corresponding to the monitored physical motion; and
 a processor configured to:
  receive the MMG signal;
  determine, from the received MMG signal, if the physical motion of the muscle is an artificially induced neuromuscular response that is attributable to an applied electrical stimulus, wherein the determination is made via a wavelet analysis; and
  provide an indication to a user if it is determined that the physical motion of the muscle is determined to be an artificially induced neuromuscular response.

Clause 22. The system of clause 21, further comprising a selectively electrifiable nerve stimulator for applying an electrical stimulus to a nerve or nerve root of the subject during a surgical procedure, the nerve stimulator including:
 an elongate body with a handle and/or handle connector at a proximal end portion and a stimulator tip at a distal end portion, the handle connector and stimulator tip being electrically conductive and in electrical communication with each other, and the exterior surface of the body between the handle connector and the stimulator tip being non-conductive, the stimulator tip including an exposed electrode operative to administer the stimulus.

Clause 23. The system of clause 22, wherein the selectively electrifiable nerve stimulator is the nerve stimulator of any of clauses 1-17.

Clause 24. The system of any of clauses 21-23, wherein the processor is configured to determine if the received MMG signal is indicative of the artificially induced neuromuscular response via the wavelet analysis by applying a continuous wavelet transform to the MMG signal.

Clause 25. The system of clause 24, wherein the continuous wavelet transform is operative to:
 compare the MMG signal to a plurality of daughter wavelets;
 for each daughter wavelet, compute a convolution coefficient that is representative of a degree of similarity between the MMG signal and the daughter wavelet; and
 consolidate the plurality of computed convolution coefficients into a net-convolution coefficient by summing each of the plurality of computed convolution coefficients at each of a plurality of sequential timesteps.

Clause 26. The system of clause 25, wherein each daughter wavelet is a scaled variant of a common mother wavelet.

Clause 27. The system of clause 25, wherein the processor is further configured to identify a plurality of peaks within the net-convolution coefficient, each peak being spaced in time from a previously identified peaks by a time period.

Clause 28. The system of clause 27, wherein the applied electrical stimulus comprises a plurality of discrete electrical pulses, each pulse spaced in time from a previously administered electrical pulse by a stimulation period;
 wherein the processor is configured to determine that the physical motion of the muscle is an artificially induced neuromuscular response if the time period between identified peaks in the net-convolution coefficient matches the stimulation period between administered electrical pulses.

Clause 29. The system of any of clauses 21-28, wherein the processor is further configured to provide an indication of statistical confidence for the determination that the physical motion of the muscle is an artificially induced neuromuscular response attributable to the applied electrical stimulus.

Clause 30. The system of any of clauses 21-28 wherein the processor is further configured provide:
a control signal or indication to a robotic controller if it is determined that the physical motion of the muscle is an artificially induced neuromuscular response.

Clause 31. The system of clause 30, wherein the processor is further configured to provide the robotic controller with an indication of a statistical confidence for its determination that the physical motion of the muscle is an artificially induced neuromuscular response attributable to the applied electrical stimulus.

Clause 41. An intraoperative neural monitoring system for use during a surgical procedure, the system comprising:
a mechanical sensor configured to:
monitor a physical motion of a muscle of a subject; and
provide a mechanomyography (MMG) signal corresponding to the monitored physical motion; and
a processor configured to:
receive the MMG signal;
determine a net-convolution coefficient (NCC) via a wavelet analysis of the received MMG signal, wherein the NCC is representative of an amount of wavelet content within the MMG signal and varies as a function of time.
identify a plurality of peaks within the NCC, the plurality of peaks being spaced in time by a periodicity;
provide an alert to a user following the identification of the plurality of peaks within the NCC.

Clause 42. The system of clause 41, further comprising a selectively electrifiable nerve stimulator for applying an electrical stimulus to a nerve or nerve root of the subject during a surgical procedure, the nerve stimulator including:
an elongate body with a handle and/or handle connector at a proximal end portion and a stimulator tip at a distal end portion, the handle connector and stimulator tip being electrically conductive and in electrical communication with each other, and the exterior surface of the body between the handle connector and the stimulator tip being non-conductive, the stimulator tip including an exposed electrode operative to administer the stimulus.

Clause 43. The system of clause 42, wherein the selectively electrifiable nerve stimulator is the nerve stimulator of any of clauses 1-17.

Clause 44 The system of any of clauses 42-43, wherein the processor is further configured to selectively electrify the electrode at a stimulus periodicity; and wherein the processor is configured to provide the alert to the user if the periodicity of the identified peaks within the NCC is about equal to the stimulus periodicity.

Clause 45. The system of clause 44, wherein the stimulus periodicity is a variable frequency periodicity.

Clause 46. The system of clause 44, wherein the stimulus periodicity is a constant periodicity.

Clause 47. The system of any one of clauses 41-46, wherein the processor is further configured to provide an indication of confidence to the user corresponding to the number of identified peaks within the NCC at the periodicity, wherein the indication of confidence increases with a greater number of identified peaks at the periodicity.

Clause 48. The system of clause 47, wherein the indication of confidence is expressed via at least one of a numeric representation or a graphical representation.

Clause 49. The system of any of clauses 47-48, wherein the processor is further configured to provide an indication of a confidence lock following the identification of four or more peaks within the NCC at the periodicity.

Clause 50. The system of any one of clauses 41-49, wherein the processor is configured to determine the NCC by performing at least one of a continuous wavelet transform or a discrete wavelet transform on the MMG signal.

Clause 51. The system of any one of clauses 41-50, wherein the alert to the user comprises an indication to a user that the physical motion of the muscle is an artificially induced neuromuscular response.

Clause 52. The system of any one of claims 41-51, wherein the processor is further configured to provide a control signal to a robotic surgical system following the identification of the plurality of peaks within the NCC.

Clause 53. The system of clause 52, wherein the control signal further comprises an indication of the number of identified peaks within the NCC at the periodicity.

Clause 54. The system of any of clauses 52-53, wherein the processor is further configured to provide the robotic controller with an indication of a statistical confidence that the identified plurality of peaks within the NCC are representative of an artificially induced neuromuscular response attributable to an applied electrical stimulus.

Clause 55. The method performed by the processor in any of clauses 21-31 or 41-54.

Clause 56. A method of alerting a user to the existence of an artificially induced neuromuscular response, the method comprising:
generating a mechanomyography output signal corresponding to a mechanical motion of a muscle of a subject, the generating performed by a mechanical sensor in physical communication with the muscle;
applying a wavelet transform to the mechanomyography output signal to determine a convolution coefficient for each of a plurality of wavelets, wherein each wavelet of the plurality of wavelets is a time-scaled variant of a common mother wavelet, and wherein the convolution coefficient is indicative of a similarity between the wavelet and the mechanomyography output signal;
summing the convolution coefficients determined across the plurality of wavelets at each timestep across a plurality of timesteps to generate a net-convolution coefficient (NCC);
identifying one or more peaks in the NCC via a peak finding algorithm;
alerting a user of an following the identification of one or more peaks in the NCC.

Clause 57. The method of clause 56, wherein the one or more peaks in the NCC is a plurality of peaks in the NCC and the alerting occurs only after the identification of the plurality of peaks in the NCC.

Clause 58. The method of clause 57, further comprising determining a periodicity of the plurality of peaks in the NCC;
comparing the periodicity of the plurality of peaks in the NCC to a periodicity of an applied electrical stimulus; and alerting the user of the artificially induced neuromuscular response only if the periodicity of the plurality of peaks in the NCC is about equal to the periodicity of the applied electrical stimulus.

Clause 59. The method of any of clauses 56-58, further comprising providing an indication of a degree of statistical confidence with the alert of the artificially induced neuromuscular response; wherein the degree of statistical confidence corresponds to at least the positive predictive value of the alert.

Clause 60. The method of clause 59, further comprising refining the degree of statistical confidence following the identification of an additional peak in the NCC; and providing an indication of the refined degree of statistical confidence.

Clause 61. The method of any of clauses 56-60 further comprising determining a minimum stimulus current required to result in an identified peak in the NCC; and displaying the minimum stimulus current to the user.

Clause 62. The method of clause 61, wherein determining a minimum stimulus current comprises:
- transmitting an electrical stimulus to an electrode of a selectively electrifiable nerve stimulator, the nerve stimulator operative to apply an electrical stimulus to a nerve or nerve root during a surgical procedure, the electrical stimulus comprising a plurality of discrete electrical pulses, each having a current magnitude greater than the minimum stimulus current required to result in an identified peak in the NCC;
- identifying a plurality of peaks in the NCC corresponding to the transmitted electrical stimulus, the plurality of peaks in the NCC having a periodicity that is about equal to a periodicity of the plurality of discrete electrical pulses;
- transmitting an electrical stimulus comprising a second plurality of discrete electrical pulses following the identification of the plurality of peaks, wherein each discrete electrical pulse in the second plurality of discrete electrical pulses has a different current magnitude; and
- wherein the current magnitude of each of the discrete electrical pulse in the second plurality of discrete electrical pulses is selected to identify a current sub-range that contains the minimum stimulus current, wherein the current sub-range is defined by a first current magnitude lower than the minimum stimulus current and a second current magnitude that is greater than the minimum stimulus current; and
- wherein the displayed minimum stimulus current includes a current magnitude selected from the identified current sub-range.

Clause 63. The method of clause 62, wherein the identified plurality of peaks in the NCC that correspond to the transmitted electrical stimulus establish a confidence lock.

Clause 64. The method of any of clauses 56-63, wherein the method is performed by the system of any of clauses 31-41 or 41-54.

Clause 65. A method of alerting a user to the existence of an artificially induced neuromuscular response, the method comprising:
- generating a mechanomyography output signal corresponding to a mechanical motion of a muscle of a subject, the generating performed by a mechanical sensor in physical communication with the muscle;
- applying a wavelet transform to the mechanomyography output signal to determine a convolution coefficient for each of a plurality of wavelets, wherein each wavelet of the plurality of wavelets is a time-scaled variant of a common mother wavelet, and wherein the convolution coefficient is indicative of a similarity between the wavelet and the mechanomyography output signal;
- summing the convolution coefficients determined across the plurality of wavelets at each timestep across a plurality of timesteps to generate a net-convolution coefficient (NCC);
- determining a minimum stimulus current required to result in an identified peak in the NCC; and
- displaying the minimum stimulus current to the user.

Clause 66. The method of clause 65 wherein determining a minimum stimulus current comprises:
- transmitting an electrical stimulus to an electrode of a selectively electrifiable nerve stimulator, the nerve stimulator operative to apply an electrical stimulus to a nerve or nerve root during a surgical procedure, the electrical stimulus comprising a plurality of discrete electrical pulses, each having a current magnitude greater than the minimum stimulus current required to result in an identified peak in the NCC;
- identifying a plurality of peaks in the NCC corresponding to the transmitted electrical stimulus, the plurality of peaks in the NCC having a periodicity that is about equal to a periodicity of the plurality of discrete electrical pulses;
- transmitting an electrical stimulus comprising a second plurality of discrete electrical pulses following the identification of the plurality of peaks, wherein each discrete electrical pulse in the second plurality of discrete electrical pulses has a different current magnitude; and
- wherein the current magnitude of each of the discrete electrical pulse in the second plurality of discrete electrical pulses is selected to identify a current sub-range that contains the minimum stimulus current, wherein the current sub-range is defined by a first current magnitude lower than the minimum stimulus current and a second current magnitude that is greater than the minimum stimulus current; and
- wherein the displayed minimum stimulus current includes a current magnitude selected from the identified current sub-range.

Clause 67. The method of clause 66, wherein the selectively electrifiable nerve stimulator is the nerve stimulator of any of clauses 1-17.

Clause 68. The method of clause 67, further comprising contacting the nerve with the electrode of the selectively electrifiable nerve stimulator.

Clause 71. A robotic surgical system for performing a surgical procedure within the body of a subject, the robotic surgical system comprising:
- an elongate surgical instrument having a proximal end portion and a distal end portion;
- a robotic controller configured to control the motion of the distal end portion of the surgical instrument; and
- an intraoperative neural monitoring system in communication with the robotic controller, wherein the intraoperative neural monitoring system is the system of any of clauses 30-31 or 52-54 and wherein the intraoperative neural monitoring system is operative to provide the control signal to the robotic controller.

Clause 72. The robotic surgical system of clause 71, wherein the robotic controller is configured to limit the range of motion of the elongate surgical instrument in response to the received control signal.

Clause 73. The robotic surgical system of clause 71, wherein the robotic controller is configured to prevent motion of the distal end portion of the surgical instrument in response to the control signal.

Clause 74. The robotic surgical system of any one of clauses 71-73, wherein the distal end portion of the surgical instrument includes a stimulator configured to provide an electrical stimulus.

Clause 75. The robotic surgical system of any one of clauses 71-74, wherein the elongate surgical instrument includes an end effector disposed at the distal end portion, the end effector being actuatable in at least one degree of freedom; wherein the robotic controller is configured to control the actuation of the end effector; and wherein the robotic controller is configured to prevent actuation of the end effector in response to the control signal.

Clause 76. The robotic surgical system of any one of clauses 71-74, wherein the elongate surgical instrument includes an end effector disposed at the distal end portion, the end effector being actuatable in at least one degree of freedom; wherein the robotic controller is configured to control the actuation of the end effector; and wherein the robotic controller is configured to actuate the end effector in response to the control signal.

Clause 77. The robotic surgical system of any one of clauses 71-76, further comprising a master station in communication with the robotic controller and configured to: receive an input from a user corresponding to an intended movement of the distal end portion of the surgical instrument; and provide a motion command to the robotic controller corresponding to the received input; and wherein the master station is configured to provide at least one of a visual alert and auditory alert if an induced muscle response is detected.

Clause 78. The robotic surgical system of any of clauses 71-77, wherein the an intraoperative neural monitoring system is operative to perform the method of any of clauses 56-64.

Clause 81. A method of alerting a user to the existence of an artificially induced neuromuscular response in a subject, the method comprising:
generating a series of electrical stimuli at a predetermined period with an electrode disposed at a distal end portion of an elongate medical device;
detecting a series of mechanomyographic (MMG) responses of the subject using a mechanical sensor, each MMG response indicative of a contraction of a muscle of the subject;
determining a degree of statistical confidence that the detected series of MMG responses was artificially induced by the series of electrical stimuli;
outputting, to the user, both:
an alert that a series of MMG responses has been detected; and
the determined degree of statistical confidence that the detected series of MMG responses was artificially induced by the series of electrical stimuli.

Clause 82. The method of clause 81, wherein the degree of statistical confidence is a function of a quantity of MMG responses that are detected in the series of MMG responses.

Clause 83. The method of clause 81 or 82, wherein the degree of statistical confidence is a function of a periodicity of the series of MMG responses and the predetermined period of the electrical stimuli.

Clause 84. The method of any of clauses 81-83, further comprising refining the degree of statistical confidence following at least one of: the generation of an additional electrical stimuli or the detection of an additional MMG response; and
outputting, to the user, the refined degree of statistical confidence.

Clause 85. The method of any of clauses 81-84, wherein detecting a series of mechanomyographic (MMG) responses comprises:
generating a MMG output signal corresponding to a mechanical motion of a muscle of the subject, the generating performed by a mechanical sensor in physical communication with the muscle; and
applying at least one of a wavelet transform or a fast fourier transform to the MMG output signal.

Clause 86. The method of any of clauses 81-84, wherein detecting a series of mechanomyographic (MMG) responses comprises:
generating a mechanomyography (MMG) output signal corresponding to a mechanical motion of a muscle of a subject, the generating performed by a mechanical sensor in physical communication with the muscle;
applying a wavelet transform to the MMG output signal to determine a convolution coefficient for each of a plurality of daughter wavelets, wherein each daughter wavelet of the plurality of daughter wavelets is a time-scaled variant of a common mother wavelet, and wherein the convolution coefficient is indicative of a similarity between the daughter wavelet and the MMG output signal;
summing the convolution coefficients determined across the plurality of daughter wavelets at each timestep across a plurality of timesteps to generate a net-convolution coefficient (NCC) that varies across the plurality of timesteps;
identifying one or more peaks in the NCC via a peak finding algorithm, and wherein each of the one or more peaks in the NCC is a MMG response of the series of MMG responses.

Clause 87. The method of clause 86, wherein determining a minimum stimulus current comprises:
transmitting the series of electrical stimuli to an electrode of a selectively electrifiable nerve stimulator, the nerve stimulator operative to apply an electrical stimulus to a nerve or nerve root during a surgical procedure, the series of electrical stimuli comprising a plurality of discrete electrical pulses, each having a current magnitude greater than the minimum stimulus current required to result in an identified peak in the NCC;
identifying a plurality of peaks in the NCC corresponding to the transmitted electrical stimulus, the plurality of peaks in the NCC having a periodicity that is about equal to a periodicity of the plurality of discrete electrical pulses;
transmitting a second series of electrical stimuli to the electrode, the second series of electrical stimuli comprising a second plurality of discrete electrical pulses, and the transmitting occurring following the identification of the plurality of peaks, wherein each discrete electrical pulse in the second plurality of discrete electrical pulses has a different current magnitude; and
wherein the current magnitude of each of the discrete electrical pulse in the second plurality of discrete electrical pulses is selected to identify a current sub-range that contains the minimum stimulus current, wherein the current sub-range is defined by a first current magnitude lower than the minimum stimulus current and a second current magnitude that is greater than the minimum stimulus current; and
wherein the minimum stimulus current includes a current magnitude selected from the identified current sub-range.

Clause 88. The method of clause 86, wherein the identified plurality of peaks in the NCC that correspond to the transmitted electrical stimulus establish a confidence lock, the method further comprising displaying an indication of the confidence lock via a display.

Clause 89 The method of any one of clauses 81-88, further comprising determining, via a processor, a minimum stimulus current required to induce a detectable MMG response from the muscle via the electrical stimulus.

Clause 90. The method of clause 89, wherein:
the minimum stimulus current is determined by iteratively adjusting the current of each electrical stimulus and monitoring for an induced MMG response, the iterative adjustment being performed by an algorithmic targeting technique to minimize the number of iterative steps.

Clause 91. The method of clause 90, further comprising:
using a confidence lock scheme to identify the minimum stimulus current, the confidence lock scheme maintaining a high-confidence lock on the identified minimum stimulus current when following a decrease in current an MMG response is not detected, provided that the MMG response returns when the current is increased in the next stimulus.

Clause 92. A method of intraoperative neural monitoring in a surgical procedure, the method comprising:
generating a series of electrical stimuli at a predetermined period with an electrode disposed at a distal end portion of an elongate medical device;
generating a mechanomyography (MMG) output signal corresponding to a mechanical motion of a muscle of the subject, the generating performed by a mechanical sensor in physical communication with the muscle;
analyzing the MMG output signal to identify one or more MMG events, each MMG event being indicative of an artificially induced neuromuscular response of the muscle in response to an electrical stimuli of the series of electrical stimuli;
determining a level of statistical confidence that the identified one or more MMG events were caused by the electrical stimuli; and
providing an alert to a user that includes the level of statistical confidence and an indication of detected MMG events; and
wherein the level of statistical confidence is a function of a quantity of sequential identified MMG events and an algorithm used to identify the one or more MMG events.

Clause 93 The method of clause 92, wherein the level of statistical confidence is further a function of a comparison of a periodicity of the detected MMG events and the predetermined period of the electrical stimuli.

Clause 94. The method of clause 92 or 93, further comprising refining the degree of statistical confidence following at least one of: the generation of an additional electrical stimuli or the detection of an additional MMG response; and
providing, to the user, the refined degree of statistical confidence.

Clause 95. The method of any of clauses 92-94, wherein analyzing the MMG output signal to identify one or more MMG events comprises:

applying a wavelet transform to the MMG output signal to determine a convolution coefficient for each of a plurality of daughter wavelets, wherein each daughter wavelet of the plurality of daughter wavelets is a time-scaled variant of a common mother wavelet, and wherein the convolution coefficient is indicative of a similarity between the daughter wavelet and the MMG output signal;
summing the convolution coefficients determined across the plurality of daughter wavelets at each timestep across a plurality of timesteps to generate a net-convolution coefficient (NCC) that varies across the plurality of timesteps;
identifying one or more peaks in the NCC via a peak finding algorithm, and wherein each of the one or more peaks in the NCC is an MMG event.

Clause 96. The method of clause 95, wherein analyzing the MMG output signal to identify one or more MMG events further comprises applying a fast fourier transform to the MMG output signal following the identification of four or more peaks in the NCC.

Clause 97. The method of any of clauses 92-95, further comprising determining a minimum threshold current required to elicit an identifiable MMG event from the MMG output signal, the minimum threshold current being determined by iteratively adjusting the current of each electrical stimulus and monitoring for an induced MMG event.

Clause 98. The method of clause 97, wherein the iterative adjustment of the current of each electrical stimulus is controlled by an algorithmic targeting technique to minimize the number of iterative steps.

Clause 99. The method of any of clauses 92-98, wherein the alert is visually represented on a display as a bar chart, a number, a gauge, or a dial, and wherein the visual representation provides an indication of the relative degree of statistical confidence in the detected MMG events.

Clause 100. The method of any of clauses 92-99, further comprising using the detected MMG events and the corresponding level of statistical confidence to inform control dynamics of a robotic surgical system such that the robotic surgical system is operative to implement preventive measures to slow or halt the motion of a robotically controlled end effector upon an identification of an MMG event with a threshold level of statistical confidence.

Clause 101. The method of any of clauses 81-100, wherein the method is performed by the system of any of clauses 31-41 or 41-54

The invention claimed is:
1. An intraoperative neural monitoring system for use during a surgical procedure on a subject, the system comprising:
a selectively electrifiable nerve stimulator for applying an electrical stimulus to a nerve or nerve root of the subject during a surgical procedure, the nerve stimulator including:
an elongate body with a handle and/or handle connector at a proximal end portion and a stimulator tip at a distal end portion, the handle connector and stimulator tip being electrically conductive and in electrical communication with each other, and an exterior surface of the body between the handle connector and the stimulator tip being non-conductive, the stimulator tip including an exposed electrode operative to apply the electrical stimulus; and
wherein the applied electrical stimulus comprises a plurality of discrete electrical pulses, each pulse spaced in time from a previously administered electrical pulse by a stimulation period;
a mechanical sensor configured to:
   monitor a physical motion of a muscle of the subject; and
   provide a mechanomyography (MMG) signal corresponding to the monitored physical motion; and
a processor configured to:
   receive the MMG signal;
   for each wavelet of a plurality of wavelets, compute a convolution coefficient that is representative of a degree of similarity between the MMG signal and the wavelet;
   consolidate the computed convolution coefficient from each wavelet into a single net-convolution coefficient at each of a plurality of sequential timesteps;
   identify a plurality of peaks within the net-convolution coefficient, each peak being spaced in time from a previously identified peak by a time period;
   determine that the physical motion of the muscle is an artificially induced neuromuscular response attributable to the applied electrical stimulus if the time period between identified peaks in the net-convolution coefficient matches the stimulation period between administered electrical pulses; and
   provide an indication to a user if it is determined that the monitored physical motion of the muscle is an artificially induced neuromuscular response.

2. The system of claim 1, wherein the elongate body extends along a central body axis and the stimulator tip including the electrode is pitched away from the central body axis by an angle of between about 30 degrees and about 60 degrees;
   wherein the elongate body, between the distal end portion and the proximal end portion includes a tapered cross-sectional profile that transitions from a first diameter at a first location near the proximal end portion of about 1.8 mm to about 2.2 mm to a second diameter at a second near the distal end portion of about 0.7 mm to about 0.9 mm.

3. The system of claim 1 wherein each daughter wavelet is a scaled variant of a common mother wavelet.

4. The system of claim 1, wherein the processor is further configured to provide an indication of statistical confidence for the determination that the physical motion of the muscle is an artificially induced neuromuscular response attributable to the applied electrical stimulus.

5. The system of claim 1 wherein the processor is further configured provide:
   a control signal or indication to a robotic controller if it is determined that the physical motion of the muscle is an artificially induced neuromuscular response.

6. The system of claim 5, wherein the processor is further configured to provide the robotic controller with an indication of a statistical confidence for its determination that the physical motion of the muscle is an artificially induced neuromuscular response attributable to the applied electrical stimulus.

7. The system of claim 1, wherein the stimulation period is a variable stimulation period.

8. The system of claim 1, wherein the processor is further configured to:
   apply a Fourier Transform to the MMG signal to convert the MMG signal from the time domain into the frequency domain;
   determine that the physical motion of the muscle is an artificially induced neuromuscular response attributable to the applied electrical stimulus if MMG signal in the frequency domain includes a frequency peak equal to the stimulation period.

* * * * *